United States Patent [19]

Klausener et al.

[11] Patent Number: 5,412,100
[45] Date of Patent: May 2, 1995

[54] FUNGICIDAL SUBSTITUTED ACRYLIC ESTERS

[75] Inventors: Alexander Klausener, Stolberg; Gerd Kleefeld, Duesseldorf; Wilhelm Brandes, Leichlingen; Stefan Dutzmann, Duesseldorf; Gerd Hänssler, Leverkusen, all of Germany

[73] Assignee: Bayer Aktiengesellschaft, Leverkusen, Germany

[21] Appl. No.: 86,601

[22] Filed: Jul. 1, 1993

Related U.S. Application Data

[62] Division of Ser. No. 788,007, Nov. 5, 1991, Pat. No. 5,254,693, which is a division of Ser. No. 478,119, Feb. 2, 1990, Pat. No. 5,114,959.

[30] Foreign Application Priority Data

Feb. 20, 1989 [DE] Germany ............... 39 05 119.6

[51] Int. Cl.⁶ .................. C07D 277/42; C07D 263/48
[52] U.S. Cl. .................... 548/187; 548/194; 548/229; 548/231; 548/232; 548/233; 548/234
[58] Field of Search ............ 548/187, 194, 229, 231, 548/232, 233, 234

[56] References Cited

U.S. PATENT DOCUMENTS

| | | | |
|---|---|---|---|
| 4,968,709 | 11/1990 | Kleefeld | 514/370 |
| 5,000,775 | 3/1991 | Grabiak | 71/88 |
| 5,114,959 | 5/1992 | Klausener | 71/90 |

FOREIGN PATENT DOCUMENTS 3807727 9/1989 Germany ............... 71/92

OTHER PUBLICATIONS

Fleischmann, Arzneim–Forsch 39 743 (1989).
Islip, J. Med. Chem. 15(9) 951 (1972).
J. Chem. Soc. Perkin Trans. I 1986, pp. 39–59.

*Primary Examiner*—Robert Gerstl
*Attorney, Agent, or Firm*—Sprung Horn Kramer & Woods

[57] ABSTRACT

Fungicidal substituted acrylic esters of the formula

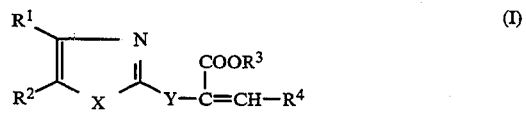
(I)

in which $R^1$ represents hydrogen, alkyl or alkenyl, or represents in each case optionally substituted aralkyl, aralkenyl, aryl or heteroaryl, $R^2$ represents halogen, cyano, nitro, formyl, halogenoalkyl, alkoxyalkyl or alkylthioalkyl, or represents hydroximinoalkyl, alkoximinoalkyl, N-alkyliminoalkyl, N-aryliminoalkyl or N,N-dialkylhydrazonoalkyl, or represents alkoxy, alkylthio, halogenoalkoxy or halogenoalkylthio, or represents aryloxy or arylthio, or represents alkanoyl, alkoxycarbonyl, N,N-dialkylcarbamoyl or heterocyclylcarbonyl, $R^3$ represents alkyl, or represents optionally substituted aralkyl, $R^4$ represents dialkylamino or represents a radical —Z—$R^5$, X represents oxygen or sulphur and Y represents oxygen or sulphur or represents a radical

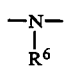

where $R^5$ represents alkyl or represents optionally substituted aralkyl, $R^6$ represents hydrogen, alkyl or alkanoyl, or represents in each case optionally substituted aralkyl or aryl, and Z represents oxygen or sulphur.

11 Claims, No Drawings

FUNGICIDAL SUBSTITUTED ACRYLIC ESTERS

This is a division of application Ser. No. 07/788,007, filed Nov. 5, 1991, now U.S. Pat. No. 5,250,693, which is a division of application Ser. No. 07 478,119, filed Feb. 2, 1990, now U.S. Pat. No. 5,114,959.

The invention relates to new substituted acrylic esters, to several processes for their preparation, to their use in pesticides and to new intermediates.

It is known that certain substituted acrylic esters, such as, for example, the compound methyl 3-methoxy-2-(2-methylpheny)-acrylate, have fungicidal properties (cf., for example, EP 178,826).

However, the activity of these previously known compounds is not entirely satisfactory in all fields of application, in particular at lower application rates and lower concentrations.

New substituted acrylic esters of the general formula (I)

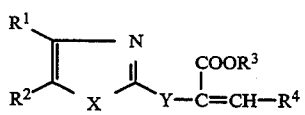
(I)

in which

R$^1$ represents hydrogen, alkyl or alkenyl, or represents in each case optionally substituted aralkyl, aralkenyl, aryl or heteroaryl, R$^2$ represents halogen, cyano, nitro, formyl, halogenoalkyl, alkoxyalkyl or alkylthioalkyl, or represents hydroximinoalkyl, alkoximinoalkyl, N-alkyliminoalkyl, N-aryliminoalkyl or N,N-dialkylhydrazonoalkyl, or represents alkoxy, alkylthio, halogenoalkoxy or halogenoalkylthio, or represents aryloxy or arylthio, or represents alkanoyl, alkoxycarbonyl, N,N-dialkylcarbamoyl or heterocyclylcarbonyl, R$^3$ represents alkyl, or represents optionally substituted aralkyl, R$^4$ represents dialkylamino or represents a radical —Z—R$^5$, X represents oxygen or sulphur and Y represents oxygen or sulphur or represents a radical

where

R$^5$ represents alkyl or represents optionally substituted aralkyl,

R$^6$ represents hydrogen, alkyl or alkanoyl, or represents in each case optionally substituted aralkyl or aryl, and Z represents oxygen or sulphur, have been found.

The compounds of the formula (I) can be present as geometric isomers or isomer mixtures of various compositions. The invention covers both the pure isomers and the isomer mixtures.

Furthermore, it has been found that the new substituted acrylic esters of the general formula (I)

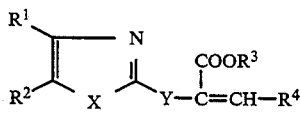
(I)

in which

R$^1$ represents hydrogen, alkyl or alkenyl, or represents in each case optionally substituted aralkyl, aralkenyl, aryl or heteroaryl, R$^2$ represents halogen, cyano, nitro, formyl, halogenoalkyl, alkoxyalkyl or alkylthioalkyl, or represents hydroximinoalkyl, alkoximinoalkyl, N-alkyliminoalkyl, N-aryliminoalkyl or N,N-dialkylhydrazonoalkyl, or represents alkoxy, alkylthio, halogenoalkoxy or halogenoalkylthio, or represents aryloxy or arylthio, or represents alkanoyl, alkoxycarbonyl, N,N-dialkylcarbamoyl or heterocyclylcarbonyl, R$^3$ represents alkyl, or represents optionally substituted aralkyl, R$^4$ represents dialkylamino or represents a radical —Z—R$^5$, X represents oxygen or sulphur and Y represents oxygen or sulphur or represents a radical

where

R$^5$ represents alkyl or represents optionally substituted aralkyl,

R$^6$ represents hydrogen, alkyl or alkanoyl, or represents in each case optionally substituted aralkyl or aryl, and Z represents oxygen or sulphur, are obtained by one of the processes described below:

(a) substituted acrylic esters of the formula (Ia)

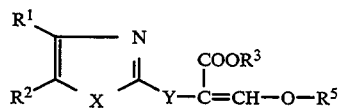
(Ia)

in which

R$^1$, R$^2$, R$^3$, R$^5$ X and Y have the abovementioned meanings, are obtained when hydroxyacrylic esters or their alkali metal salts of the formula (II)

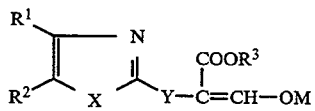
(II)

in which

M represents hydrogen or represents an alkali metal cation and

R$^1$, R$^2$, R$^3$, X and Y have the abovementioned meanings, are reacted with alkylating agents of the formula (III)

(III)

in which $E^1$ represents an electron-withdrawing leaving group and $R^5$ has the abovementioned meaning, if appropriate in the presence of a diluent and if appropriate in the presence of a reaction auxiliary;

(b) substituted acrylic esters of the formula (Ib)

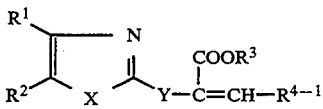
(Ib)

in which $R^{4-1}$ have represents dialkylamino and $R^1$, $R^2$, $R^3$, X and Y have the abovementioned meanings, are obtained when substituted acetic esters of of the formula (IV)

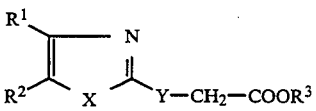
(IV)

in which $R^1$, $R^2$, $R^3$, X and Y have the abovementioned meanings, are reacted with formamides of the formula (Va)

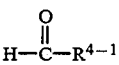
(Va)

in which $R^{4-1}$ has the abovementioned meaning, or with their derivatives of the formula (Vb)

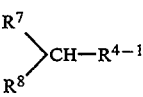
(Vb)

in which $R^7$ and $R^8$ independently of one another in each case represent alkoxy or dialkylamino and $R^{4-1}$ has the abovementioned meaning, if appropriate in the presence of a diluent;

(c) substituted acrylic esters of the formula (Ic)

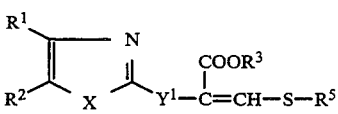
(Ic)

in which $Y^1$ represents sulphur or represents a radical

and $R^1$, $R^2$, $R^3$, $R^5$, $R^6$ and X have the abovementioned meanings, are obtained when oxalic acid derivatives of the formula (VI)

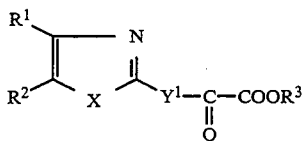
(VI)

in which $R^1$, $R^2$, $R^3$, X and $Y^1$ have the abovementioned meanings, are reacted with organometal compounds of the formula (VII)

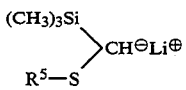
(VII)

in which $R^5$ has the abovementioned meaning, if appropriate in the presence of a diluent;

(d) substituted acrylic esters of the formula (Id)

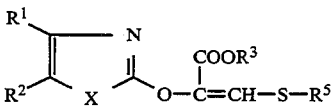
(Id)

in which $R^1$, $R^2$, $R^3$, $R^5$ and X have the abovementioned meanings, are obtained when substituted acrylic esters of the formula (VIII)

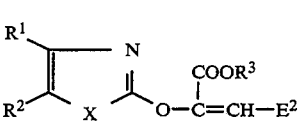
(VIII)

in which $E^2$ represents an electron-withdrawing leaving group and $R^1$, $R^2$, $R^3$ and X have the abovementioned meanings, are reacted with thiols of the formula (IX)

$R^5$-SH (IX)

in which $R^5$ has the abovementioned meaning, if appropriate in the presence of a diluent and if appropriate in the presence of a reaction auxiliary.

Finally, it has been found that the new substituted acrylic esters of the general formula (I) have a good action against pests.

Surprisingly, the substituted acrylic esters of the general formula (I) according to the invention show, for example, a considerably better fungicidal activity than the acrylic esters known from the prior art, such as, for example, the compound methyl 3-methoxy-2-(2-methyl-phenyl)-acrylate, which are compounds of a similar chemical structure and a similar type of action.

Formula (I) provides a general definition of the substituted acrylic esters according to the invention. Preferred compounds of the formula (I) are those in which $R^1$ represents hydrogen, or represents straight-chain or branched alkyl having 1 to 8 carbon atoms, or represents straight-chain or branched alkenyl having 2 to 8 carbon atoms, or represents aralkyl having 1 to 6 carbon atoms in the straight-chain or branched alkyl moiety, aralkenyl having 2 to 6 carbon atoms in the straight-chain or branched alkenyl moiety or aryl having 6 to 10 carbon atoms in the respective aryl moiety, each of which is optionally monosubstituted to polysubstituted in the aryl moiety by identical or different substituents, suitable aryl substitutents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, double-linked alkanediyl having 3 to 5 carbon atoms, or aryl, aralkyl, aryloxy or aralkyloxy, each of which has 6 to 10 carbon atoms in the aryl moiety and if appropriate 1 to 4 carbon atoms in the straight-chain or branched alkyl moiety and each of which is optionally monosubstituted to polysubstituted in the aryl moiety by identical or different substituents from the series comprising halogen, alkyl, alkoxy, alkylthio, halogenoalkyl, halogenoalkoxy or halogenoalkylthio, each of which has 1 to 4 carbon atoms and if appropriate 1 to 9 identical or different halogen atoms, or represents heteroarylalkyl or heteroaryl, each of which has 2 to 9 carbon atoms and 1 to 4 identical or different hetero atoms—in particular nitrogen, oxygen and/or sulphur—in the heteroaryl moiety and if appropriate 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and if appropriate 1 to 9 identical or different halogen atoms;

$R^1$ furthermore represents a heteroaryl radical having 2 to 9 carbon atoms and 1 to 4 identical or different hetero atoms—in particular nitrogen, oxygen and/or sulphur—which is optionally monosubstituted to polysubstituted by identical or different substituents, suitable substituents being the abovementioned aryl substituents, $R^1$ represents fluorine, chlorine, bromine, iodine, cyano, nitro or formyl, or represents straight-chain or branched halogenoalkyl having 1 to 4 carbon atoms and 1 to 9 identical or different halogen atoms, in particular fluorine, chlorine, bromine or iodine, or represents in each case straight-chain or branched alkoxyalkyl or alkylthioalkyl, each of which has 1 to 4 carbon atoms in the individual alkyl moieties, or represents in each case straight-chain or branched hydroximinoalkyl, alkoximinoalkyl, N-alkyliminoalkyl or N,N-dialkylhydrazonoalkyl, each of which has 1 to 4 carbon atoms in the individual alkyl moieties, or represents in each case straight-chain or branched alkoxy or alkylthio, each of which has 1 to 4 carbon atoms, or represents in each case straight-chain or branched halogenoalkoxy or halogenoalkylthio, each of which has 1 to 4 carbon atoms and each of which has 1 to 9 identical or different halogen atoms, in particular fluorine, chlorine or bromine, or represents in each case straight-chain or branched alkanoyl, alkoxycarbonyl or N,N-dialkylcarbamoyl, each of which has 1 to 4 carbon atoms in the individual alkyl moieties, or represents heterocyclylcarbonyl, a possible heterocyclyl radical being a saturated 5- to 7-membered N-linked heterocyclic ring which can optionally contain a further hetero atom, in particular oxygen, sulphur or nitrogen, and which can optionally be monosubstituted to tetrasubstituted by methyl and/or ethyl;

$R^2$ furthermore represents N-aryliminoalkyl, aryloxy or arylthio, each of which is optionally monosubstituted to polysubstituted in the aryl moiety by identical or different substituents, each of which has 6 to 10 carbon atoms, the straight-chain or branched alkyl moiety having 1 to 4 carbon atoms and possible aryl substituents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, or phenyl which is optionally monosubstituted to polysubstituted by identical or different substituents from the series comprising halogen and/or straight-chain or branched alkyl having 1 to 4 carbon atoms, $R^3$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted to polysubstituted in the aryl moiety by identical or different substituents, possible aryl substituents being those mentioned in the case of $R^1$, $R^4$ represents dialkylamino having in each case 1 to 6 carbon atoms in the individual straight-chain or branched alkyl moieties, or represents a radical $-Z-R^5$, X represents oxygen or sulphur and Y represents oxygen or sulphur or represents a radical

where $R^5$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted to polysubstituted in the aryl moiety by identical or different substituents, possible aryl substituents being those mentioned in the case of $R^1$, $R^6$ represents hydrogen, or represents straight-chain or branched alkyl having 1 to 6 carbon atoms, or represents straight-chain or branched alkanoyl having 1 to 6 carbon atoms in the alkyl moiety, or represents aralkyl which has 1 to 6 carbon atoms in the straight-chain or branched alkyl moiety or aryl having in each case 6 to 10 carbon atoms in the respective aryl moiety, each of these aralkyl or aryl moieties being optionally monosubstituted to polysubstituted in the aryl moiety by identical or different substituents, possible substituents in the aryl moiety in each case being those mentioned in the case of $R^1$, and Z represents oxygen or sulphur.

Particularly preferred compounds of the formula (I) are those in which $R^1$ represents hydrogen, methyl, ethyl, n- or i-propyl or n-, i-, s- or t-butyl, or represents allyl or n- or i-butenyl, or represents benzyl, phenylethyl, phenylethenyl, phenyl, naphthyl, pyridyl, thienyl or furyl, each of which is optionally monosubstituted to tetrasubstituted in the aryl moiety or in the heteroaryl moiety by identical or different substituents, possible substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoxyiminomethyl, ethoximinomethyl, methoxyiminoethyl, ethoximinoethyl, cyclopentyl, cyclohexyl, 1,3-propanediyl or 1,4-butanediyl, or phenyl, benzyl, phenoxy or benzyloxy, each of which is optionally monosubstituted to trisubstituted in the phenyl moiety by identical or different substituents from the series comprising fluorine, chlorine, bromine, methyl, ethyl, methoxy, ethoxy, methylthio, trifluoromethyl, difluoromethoxy, trifluoromethoxy and/or trifluoromethylthio, $R^2$ represents chlorine, bromine, iodine, cyano, nitro, formyl, chloromethyl, bromomethyl, iodomethyl, methoxymethyl, ethoxymethyl, n- or i-propoxymethyl, methylthiomethyl, ethylthiomethyl or n- or i-propylthiomethyl, or represents hydroximinomethyl, hydroximinoethyl or hydroximinopropyl, or represents methoximinomethyl, ethoximinomethyl, n- or i-propoximinomethyl, methoximinoethyl, ethoximinoethyl or n- or i-propoximinoethyl, or represents methyliminomethyl, ethyliminomethyl or n- or i-propyliminomethyl, or represents methyliminoethyl, ethyliminoethyl or n- or i-propyliminoethyl, or represents N,N-dimethylhydrazonomethyl, N,N-diethylhydrazonomethyl, N-methyl-N-ethylhydrazonomethyl, N-methyl-N-propylhydrazonomethyl, N,N-dipropylhydrazonomethyl, N,N-dimethylhydrazonoethyl or N,N-diethylhydrazonoethyl, or represents methoxy, ethoxy, n- or i-propoxy, methylthio, ethylthio or n- or i-propylthio, or represents trifluoromethoxy, difluoromethoxy, dichlorofluoromethoxy, difluorochloromethoxy, trichloromethoxy, trifluoromethylthio, trichloromethylthio, difluoromethylthio, dichlorofluoromethylthioordifluorochloromethylthio or represents acetyl, propionyl, butyryl, methoxycarbonyl, ethoxycarbonyl, n- or i-propoxycarbonyl, N,N-dimethylaminocarbonyl, N,N-diethylaminocarbonyl, N,N-dipropylaminocarbonyl, N-methyl-N-ethylaminocarbonyl or N-methyl-N-propylaminocarbonyl, or represents 1-piperidinylcarbonyl or 4-morpholinylcarbonyl, or represents N-phenyliminomethyl, N-phenyliminoethyl, phenoxy or phenylthio, each of which is optionally monosubstituted to trisubstituted in the phenyl moiety by identical or different substituents, possible substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoximinomethyl, ethoximinomethyl, methoximinoethyl or ethoximinoethyl, or phenyl which is optionally monosubstituted to trisubstituted by identical or different substituents from the series comprising fluorine, chlorine, bromine, methyl and/or ethyl, $R^3$ represents methyl, ethyl, n- or i-propyl or n-, i-, s- or t-butyl, or represents benzyl which is optionally monosubstituted to trisubstituted by identical or different substituents, possible substituents being those mentioned in the case of $R^1$, $R^4$ represents dialkylamino having in each case 1 to 4 carbon atoms in the individual straight-chain or branched alkyl moieties, or represents a radical —Z—$R^5$, X represents oxygen or sulphur and Y represents oxygen or sulphur, or represents a radical

where $R^5$ represents methyl, ethyl, n- or i-propyl or n-, i-, s- or t-butyl, or represents benzyl which is optionally monosubstituted to trisubstituted by identical or different substituents, possible substituents being those mentioned in the case of $R^1$;

$R^6$ represents hydrogen, methyl, ethyl, n- or i-propyl or n-, i-, s- or t-butyl, or represents acetyl, propionyl or n- or i-butyryl, or represents benzyl or phenyl, each of which is optionally monosubstituted to trisubstituted by identical or different substituents, possible substituents being those mentioned in the case of $R^1$, and Z represents oxygen or sulphur.

Very particularly preferred compounds of the formula (I) are those in which $R^1$ represents hydrogen, methyl, ethyl, or n- or i-propyl, or represents phenyl or naphthyl, each of which is optionally monosubstituted to tetrasubstituted by identical or different substituents, possible substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl or 1,4-butanediyl, or phenyl, phenoxy, benzyl or benzyloxy, each of which is optionally monosubstituted or disubstituted by identical or different substituents from the series comprising fluorine, chlorine, bromine, methyl and/or ethyl, $R^2$ represents chlorine, bromine, cyano, nitro, formyl, methoxymethyl, ethoxymethyl, methylthiomethyl, hydroximinomethyl, methoximinomethyl, ethoximinomethyl, methyliminomethyl, ethyliminomethyl, N,N-dimethylhydrazonomethyl or N,N-diethylhydrazonomethyl, or represents methoxy, ethoxy, methylthio, ethylthio, trifluoromethylthio, dichlorofluoromethylthio, difluorochloromethylthio or trichloromethylthio, or represents acetyl, methoxycarbonyl, ethoxycarbonyl, N, N-d imethyl aminocarbonyl, N, N-diethylaminocarbonyl or N-methyl-N-ethylaminocarbonyl, or represents phenylthio which is optionally monosubstittuted or disubstituted by identical or different substituents, possible substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy or trifluoromethylthio, $R^3$ represents methyl, ethyl or benzyl, $R^4$ represents dimethylamino or diethylamino, or represents a radical —Z—$R^5$, X represents oxygen or sulphur and Y represents oxygen or sulphur, or represents a radical

where $R^5$ represents methyl, ethyl, n- or i-propyl or benzyl, $R^6$ represents hydrogen, methyl, ethyl, acetyl or propionyl, or represents benzyl or phenyl, each of which is optionally monosubstituted or di-substituted by identical or different substituents from the series comprising fluorine, chlorine, bromine, methyl, ethyl and/or trifluoromethyl, and Z represents oxygen or sulphur.

Especially preferred compounds of the formula (I) are those in which $R^1$ represents hydrogen, methyl, ethyl or n- or i-propyl, or represents phenyl which is optionally monosubstituted or disubstituted by identical or different substituents, possible substituents being: fluorine, chlorine, bromine, cyano, nitro, methyl, ethyl, methoxy, ethoxy, methylthio, trifluoromethyl, trifluoromethoxy, trifluoromethylthio, methoxycarbonyl, ethoxycarbonyl, methoximinomethyl, cyclopentyl, 1,3-propanediyl, methoximinoethyl or phenyl, phenoxy, benzyl or benzyloxy, each of which is optionally monosubstituted or disubstituted by identical or different substituents from the series comprising fluorine, chlorine, bromine or methyl, $R^2$ represents chlorine, bromine, cyano, nitro, formyl, methoxymethyl, methylthiomethyl, methoxycarbonyl, ethoxycarbonyl, methylthio, trifluoromethylthio or methoximinomethyl, $R^3$ represents methyl or ethyl, $R^4$ represents methoxy, ethoxy, methylthio or dimethylamino, X represents oxygen or sulphur and Y represents an N-methyl radical.

The following substituted acrylic esters of the general formula (I) may be mentioned individually in addition to the compounds mentioned in the preparation examples:

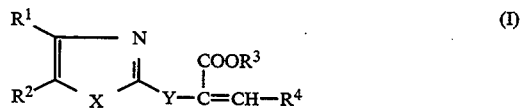

| $R^1$ | $R^2$ | $R^3$ | $R^4$ | X | Y |
|---|---|---|---|---|---|
| 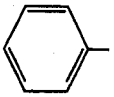 | CN | $CH_3$ | $OCH_3$ | S | N—$CH_3$ |
| 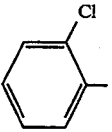 | CN | $CH_3$ | $OCH_3$ | S | N—$CH_3$ |
| 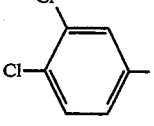 | CN | $CH_3$ | $OCH_3$ | S | N—$CH_3$ |
| 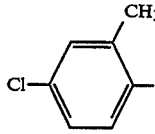 | CN | $CH_3$ | $OCH_3$ | S | N—$CH_3$ |
| 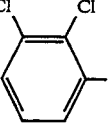 | CN | $CH_3$ | $OCH_3$ | S | N—$CH_3$ |

-continued

| R¹ | R² | R³ | R⁴ | X | Y |
|---|---|---|---|---|---|
| 2,4-dichlorophenyl | CN | CH₃ | OCH₃ | S | N—CH₃ |
| 2,5-dichlorophenyl | CN | CH₃ | OCH₃ | S | N—CH₃ |
| 2,3-dichlorophenyl | CN | CH₃ | OCH₃ | S | N—CH₃ |
| 3,4,5-trichlorophenyl | CN | CH₃ | OCH₃ | S | N—CH₃ |
| 3,5-dichlorophenyl | CN | CH₃ | OCH₃ | S | N—CH₃ |
| 2-bromophenyl | CN | CH₃ | OCH₃ | S | N—CH₃ |
| 3-bromophenyl | CN | CH₃ | OCH₃ | S | N—CH₃ |
| 2-fluorophenyl | CN | CH₃ | OCH₃ | S | N—CH₃ |
| 4-fluorophenyl | CN | CH₃ | OCH₃ | S | N—CH₃ |
| 2-chloro-4-fluorophenyl | CN | CH₃ | OCH₃ | S | N—CH₃ |

-continued

| R¹ | R² | R³ | R⁴ | X | Y |
|---|---|---|---|---|---|
| 2-Cl, 6-F-phenyl (Cl top, F bottom) | CN | CH₃ | OCH₃ | S | N—CH₃ |
| 3-O₂N, 6-Cl-phenyl | CN | CH₃ | OCH₃ | S | N—CH₃ |
| 3-OCH₃, 6-Cl-phenyl | CN | CH₃ | OCH₃ | S | N—CH₃ |
| 3-CH₃, 6-Cl-phenyl | CN | CH₃ | OCH₃ | S | N—CH₃ |
| 2-Cl, 3-CH₃O-phenyl | CN | CH₃ | OCH₃ | S | N—CH₃ |
| 2,3-(CH₃O)₂-phenyl | CN | CH₃ | OCH₃ | S | N—CH₃ |
| 2,4-(CH₃O)₂-3-OCH₃-phenyl | CN | CH₃ | OCH₃ | S | N—CH₃ |
| biphenyl-4-yl | CN | CH₃ | OCH₃ | S | N—CH₃ |
| 2-OCH₃-phenyl | CN | CH₃ | OCH₃ | S | N—CH₃ |
| 3-CH₃O-phenyl | —CHO | CH₃ | OCH₃ | S | N—CH₃ |
| 4-CH₃O-phenyl | —CHO | CH₃ | OCH₃ | S | N—CH₃ |

-continued

| R¹ | R² | R³ | R⁴ | X | Y |
|---|---|---|---|---|---|
| 4-biphenylyl | —CHO | CH₃ | OCH₃ | S | N—CH₃ |
| 2-methylphenyl | —CHO | CH₃ | OCH₃ | S | N—CH₃ |
| 3-methylphenyl | —CHO | CH₃ | OCH₃ | S | N—CH₃ |
| 4-methylphenyl | —CHO | CH₃ | OCH₃ | S | N—CH₃ |
| pyridin-2-yl | —CHO | CH₃ | OCH₃ | S | N—CH₃ |
| pyridin-3-yl | —CHO | CH₃ | OCH₃ | S | N—CH₃ |
| pyridin-4-yl | —CHO | CH₃ | OCH₃ | S | N—CH₃ |
| 6-methylpyridin-3-yl | —CHO | CH₃ | OCH₃ | S | N—CH₃ |
| naphthalen-2-yl | —COOCH₃ | CH₃ | OCH₃ | S | N—CH₃ |
| naphthalen-2-yl | —COOCH₃ | CH₃ | OCH₃ | O | N—CH₃ |
| 4-chlorophenyl | —CHO | CH₃ | OCH₃ | S | N-phenyl |
| 3,4-dichlorophenyl | —CHO | CH₃ | OCH₃ | S | N—CH₃ |
| 4-chlorophenyl | Cl | CH₃ | OCH₃ | O | N-phenyl |

-continued
| R¹ | R² | R³ | R⁴ | X | Y |
|---|---|---|---|---|---|
| 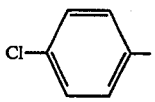 | Cl | CH₃ | OCH₃ | O | N—CH₃ |
| 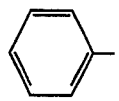 | Cl | CH₃ | OCH₃ | O | N—CH₃ |
| 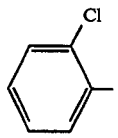 | Cl | CH₃ | OCH₃ | O | N—CH₃ |
| 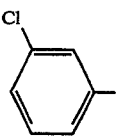 | Cl | CH₃ | OCH₃ | O | N—CH₃ |
| 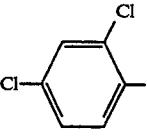 | Cl | CH₃ | OCH₃ | O | N—CH₃ |
| 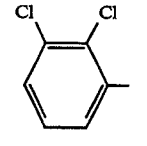 | Cl | CH₃ | OCH₃ | O | N—CH₃ |
| 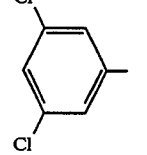 | Br | CH₃ | OCH₃ | O | N—CH₃ |
| 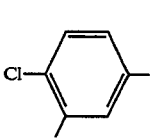 | Br | CH₃ | OCH₃ | O | N—CH₃ |
| 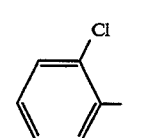 | Br | CH₃ | OCH₃ | O | N—CH₃ |
| 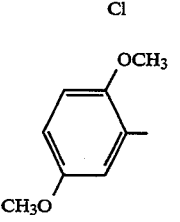 | Br | CH₃ | OCH₃ | O | N—CH₃ |

-continued

| R¹ | R² | R³ | R⁴ | X | Y |
|---|---|---|---|---|---|
| 2-methoxyphenyl | Br | CH₃ | OCH₃ | O | N—CH₃ |
| 3-methoxyphenyl | Br | CH₃ | OCH₃ | O | N—CH₃ |
| 4-methoxyphenyl | Br | CH₃ | OCH₃ | O | N—CH₃ |
| 3,5-dimethoxyphenyl | NO₂ | CH₃ | OCH₃ | O | N—CH₃ |
| 2-methylphenyl | NO₂ | CH₃ | OCH₃ | O | N—CH₃ |
| 3-methylphenyl | NO₂ | CH₃ | OCH₃ | O | N—CH₃ |
| 4-methylphenyl | NO₂ | CH₃ | OCH₃ | O | N—CH₃ |
| 4-biphenyl | —COOCH₃ | CH₃ | OCH₃ | O | N—CH₃ |
| 4-biphenyl | Br | CH₃ | OCH₃ | O | N—CH₃ |
| 4-biphenyl | Cl | CH₃ | OCH₃ | O | N—CH₃ |
| 6-methyl-3-pyridyl | —COOCH₃ | CH₃ | OCH₃ | O | N—CH₃ |
| 2-bromophenyl | —CH=N—OCH₃ | CH₃ | OCH₃ | O | N—CH₃ |

-continued

| R¹ | R² | R³ | R⁴ | X | Y |
|---|---|---|---|---|---|
| 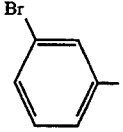 3-Br-phenyl | —CH=N—OCH₃ | CH₃ | OCH₃ | O | N—CH₃ |
| 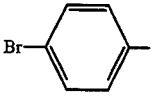 4-Br-phenyl | —CH=N—OCH₃ | CH₃ | OCH₃ | O | N—CH₃ |
| 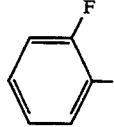 2-F-phenyl | —CH₂—OCH₃ | CH₃ | OCH₃ | O | N—CH₃ |
| 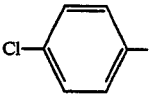 4-Cl-phenyl | —CH₂—OCH₃ | CH₃ | OCH₃ | O | N—CH₃ |
| 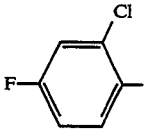 2-Cl-4-F-phenyl | —CH₂—OCH₃ | CH₃ | OCH₃ | O | N—CH₃ |
| 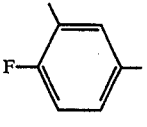 3-Cl-4-F-phenyl | —CH₂—OCH₃ | CH₃ | OCH₃ | O | N—CH₃ |
| 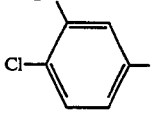 3-NO₂-4-Cl-phenyl | —CH₂—OCH₃ | CH₃ | OCH₃ | O | N—CH₃ |
| 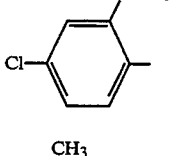 2-OCH₃-4-Cl-phenyl | —CH₂—OCH₃ | CH₃ | OCH₃ | O | N—CH₃ |
| 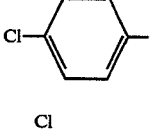 2-CH₃-4-Cl-phenyl | —CH₂—OCH₃ | CH₃ | OCH₃ | O | N—CH₃ |
| 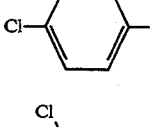 3,4-diCl-phenyl | Br | CH₃ | OCH₃ | S | N—CH₃ |
| 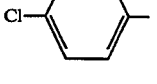 3,4-diCl-phenyl | —SCH₃ | CH₃ | OCH₃ | S | N—CH₃ |

-continued

| R¹ | R² | R³ | R⁴ | X | Y |
|---|---|---|---|---|---|
| 3,4-diCl-phenyl | —COOCH₃ | CH₃ | OCH₃ | S | N—CH₃ |
| 2,4-diCl-phenyl | —OCH₃ | CH₃ | SCH₃ | S | N—CH₃ |
| 4-Cl-phenyl | —OCH₃ | CH₃ | SCH₃ | S | N—CH₃ |
| 3,4-diCl-phenyl | NO₂ | CH₃ | OCH₃ | S | N—CH₃ |
| phenyl | —COOCH₃ | CH₃ | OCH₃ | S | N—CH₃ |
| 4-Cl-phenyl | CN | CH₃ | —N(CH₃)₂ | S | N—CH₃ |
| 2-Cl-phenyl | —CHO | CH₃ | —N(CH₃)₂ | O | N—CH₃ |
| 2,4,6-triCl-phenyl | CN | CH₃ | OCH₃ | S | S |
| 3,4-diCl-phenyl | Br | CH₃ | OCH₃ | O | S |
| 4-Cl-phenyl | —COOCH₃ | C₂H₅ | OCH₃ | S | N—CH₃ |
| 2-thienyl | —COOCH₃ | CH₃ | OCH₃ | S | N—CH₃ |
| 3-thienyl | Br | CH₃ | OCH₃ | S | N—CH₃ |

-continued

| R¹ | R² | R³ | R⁴ | X | Y |
|---|---|---|---|---|---|
| 3-methyl-2-thienyl (with CH₃) | Cl | CH₃ | OCH₃ | S | N—CH₃ |
| 2-furyl | Br | CH₃ | OCH₃ | S | N—CH₃ |
| 2-thienyl | Cl | CH₃ | OCH₃ | O | N—CH₃ |
| 3-thienyl | NO₂ | CH₃ | OCH₃ | O | N—CH₃ |
| 3-methyl-2-thienyl | —COOCH₃ | CH₃ | OCH₃ | O | N—CH₃ |
| 2-furyl | —CH₂—S—CH₃ | CH₃ | OCH₃ | O | N—CH₃ |

If, for example, methyl 2-{N-[4-(3,4-dichlorophenyl)-5-bromothiazol-2-yl-oxy]-N-methylamino}-3-hydroxyacrylate and dimethyl sulphate are used as starting materials, the course of the reaction of process (a) according to the invention may be represented by the following equation:

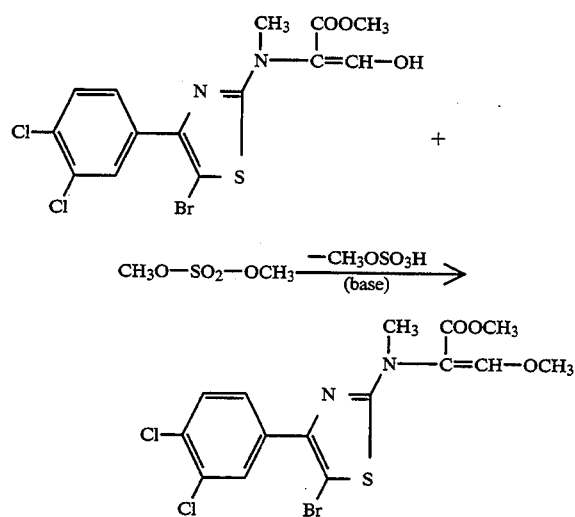

If, for example, methyl 2-[4-(4-chlorophenyl)-5-methoxycarbonylthiazol-2-yl-oxy]-acetate and dimethyl-formamide dimethylacetal are used as starting materials, the course of the reaction of process (b) according to the invention may be represented by the following equation:

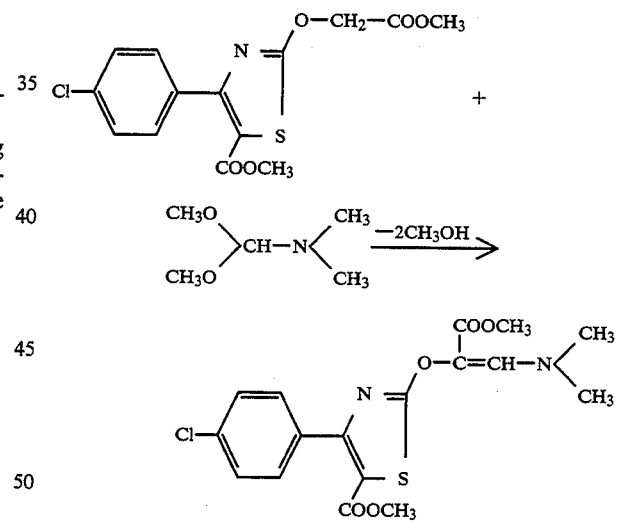

If, for example, methyl 2-[4-(2,4-dichlorophenyl)-5-chlorotriazol-2-yl-thio]-2-oxo-acetate and (methylthio)-(trimethylsilyl)-methylenelithium are used as starting substances, the course of the reaction of process (c) according to the invention may be represented by the following equation:

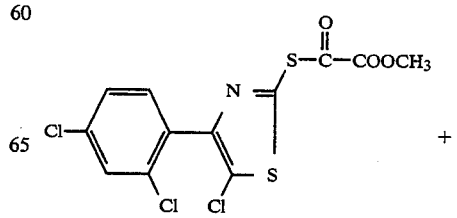

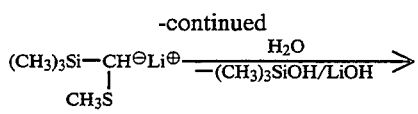

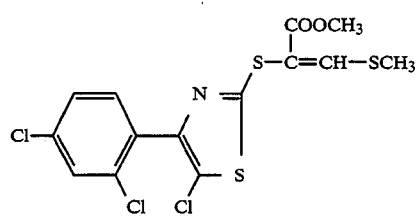

If, for example, methyl 2-[4-(4-chlorophenyl)-5-cyanooxazol-2-yl-oxy]-3-methylsulphonyloxy-acrylate and methylmercaptan are used as starting materials, the course of the reaction of process (d) according to the invention may be represented by the following equation:

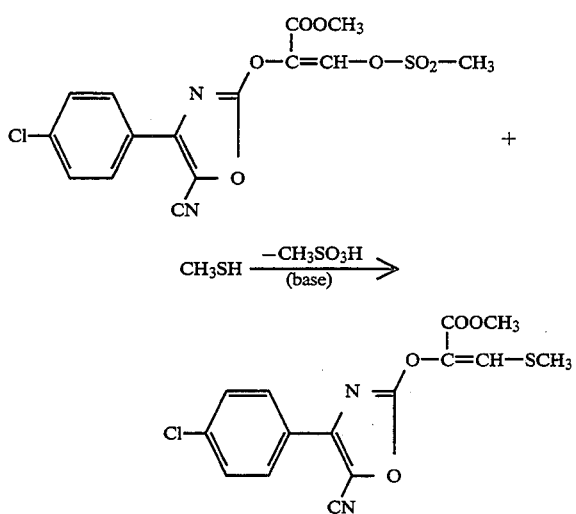

Formula (II) provides a general definition of the hydroxyacrylic esters or their alkali metal salts which are required as starting materials for carrying out process (a) according to the invention. In this formula (II) $R^1$, $R^2$, $R^3$, X and Y preferably represent those radicals which have already been mentioned in connection with the description of the substances of the formula (I) according to the invention as being preferred for these substituents.

M preferably represents hydrogen, or represents a sodium or potassium cation.

The hydroxyacrylic esters of the formula (II) were hitherto unknown and are also the subject-matter of the invention.

They are obtained when substituted acetic esters of the formula (IV)

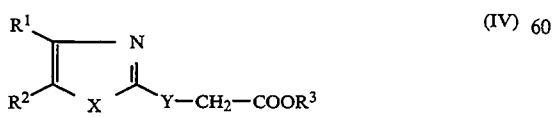

in which $R^1$, $R^2$, $R^3$, X and Y have the abovementioned meanings are reacted with formic esters of the formula (X),

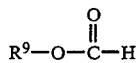

in which $R^9$ represents alkyl, in particular represents methyl or ethyl, if appropriate in the presence of a diluent, such as, for example, dimethylformamide, and if appropriate in the presence of a basic reaction auxiliary, such as, for example, sodium hydride, at temperatures between $-20°$ C. and $+50°$ C.

Formic esters of the formula (X) are generally known compounds of organic chemistry.

Formula (III) provides a general definition of the alkylating agents furthermore required as starting materials for carrying out process (a) according to the invention. In this formula (III), $R^5$ preferably represents those radicals which have already been mentioned in connection with the description of the substances of the formula (I) according to the invention as being preferred for this substituent.

$E^1$ represents a leaving group customary in alkylating agents, preferably represents an optionally substituted alkyl, alkoxy or arylsulphonyloxy radical, such as, for example, a methoxysulphonyloxy radical, an ethoxysulphonyloxy radical or a p-toluenesulphonyloxy radical, or represents halogen, or in particular represents chlorine, bromine or iodine.

The alkylating agents of the formula (III) are generally known compounds of organic chemistry.

Formula (IV) provides a general definition of the substituted acetic esters required as starting materials for carrying out process (b) according to the invention and for the synthesis of the precursors of the formula (II). In this formula (IV), $R^1$, $R^2$, $R^3$, X and Y preferably represent those radicals which have already been mentioned in connection with the description of the substances of the formula (I) according to the invention as being preferred for these substituents.

Some of the substituted acetic esters of the formula (IV) are known (cf., for example, J. Med. Chem. 5, 951–954 [1972]; J. Med. Chem. 14, 10–16 [1971]; J. Med. Chem. 14, 1030–1034 [1973]).

Substituted acetic esters of the formula (IVa)

in which $Y^2$ represents oxygen or sulphur, or represents an N-alkyl radical, preferably having 1 to 4 carbon atoms, in particular represents an —N-methyl radical or represents an —N-ethyl radical and $R^1$, $R^2$, $R^3$ and X have the abovementioned meanings, were hitherto unknown and also form a subject-matter of the invention.

They are obtained in analogy to known processes, for example when thiazole or oxazole derivatives of the formula (XIa)

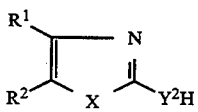

(XIa)

in which

R¹, R², X and Y² have the abovementioned meanings, or thiazole or oxazole derivatives of the formula (XIb)

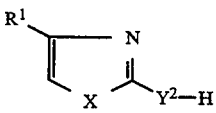

(XIb)

in which

R¹, X and Y² have the abovementioned meanings are reacted with bromoacetic esters of the formula (XII)

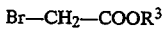

Br—CH₂—COOR³ (XII)

in which

R³ has the abovementioned meaning, if appropriate in the presence of a diluent, such as, for example, dimethylformamide, and if appropriate in the presence of a reaction auxiliary, such as, for example, sodium hydride, at temperatures between −20° C. and +150° C., and, if desired, the products are subsequently substituted in the 5-position of the thiazole or oxazole ring using customary electrophilic substitution reactions, or derivatives are formed on functional groups which are already present in this position with the aid of generally known processes (cf. also the preparation examples). For example, it is possible by customary electrophilic substitutions to introduce the nitro group using nitric acid, the halogen radicals using elemental chlorine or bromine or other customary halogenating agents, the formyl group in the Viismeier reaction using phosphorus oxychloride and dimethylformamide, alkanoyl groups in Friedel-Crafts acylations using alkanoyl chlorides in the presence of aluminum trichloride, alkylthio radicals, halogenoalkylthio radicals and arylthio radicals by direct sulphenylation using the corresponding sulphenyl chlorides, or by rhodanation using potassium thiocyanate or ammonium thiocyanate, followed by reduction to the mercapto group and alkylation thereof. Iminoalkyl substituents in the 5-position of the heterocyclic ring are obtained by reacting formyl or alkanoyl substituents with aliphatic or aromatic amines, hydroxyl amines or hydrazines, in a customary manner. Amide substituents are obtained from methoxy or ethoxycarbonyl groups by reaction with amines, the cyano group is obtained by dehydration of the resulting N-unsubstituted carbamoyl group or by dehydration of the hydroximinomethyl group. Alkoxymethyl groups, alkylthiomethyl groups and halogenomethyl groups may be introduced by reducing the formyl group, for example using sodium borohydride, followed by alkylation of the resulting hydroxymethyl group or subsequent nucleophilic substitution with halogen or subsequent sulphonylation with a customary alkylsulphonyl chloride or arylsulphonyl Chloride, followed by substitution with alcohols or thiols with the elimination of alkylsulphonyloxy or arylsulphonyloxy radicals.

If appropriate, it can also be advantageous to carry out the above-described substitution reactions and/or reactions in which derivatives are formed as early as in the stage of the thiazole or oxazole derivatives of the formulae (XIa) or (XIb), before the reaction with the bromoacetic esters of the formula (XII) takes place (cf. also the preparation examples).

Thiazole and oxazole derivatives of the formulae (XIa) and (XIb) are known or can be obtained in analogy to known processes (cf., for example, Heterocycles 23, 2645-2649 [1985]; GB 2,020,661; Indian J. Chem. Sect. B, 16B, 749-751 [1978]; J. org. Chem. 32, 3132-3134 [1967]; J. Heterocycl. Chem. 22, 1621-1630 [1985]; JP 63/112,572; JP 63/112,573; JP 63/112,574; JP 62/132,871). Bromoacetic esters of the formula (XII) are generally known compounds of organic chemistry.

Formulae (Va) and (Vb) provide general definitions of the formamides and their derivatives furthermore required as starting substances for carrying out process (b) according to the invention. In these formulae (Va) and (Vb), $R^{4-1}$ preferably represents dialkylamino having in each case 1 to 6, in particular having 1 to 4, carbon atoms in the individual straight-chain or branched alkyl moieties. $R^{4-1}$ very particularly preferably represents dimethylamino or diethylamino.

$R^7$ and $R^8$ preferably independently of one another in each case represent straight-chain or branched alkoxy having 1 to 4 carbon atoms, in particular represent methoxy or ethoxy, or represent a dialkylamino radical having in each case 1 to 6, in particular 1 to 4, carbon atoms in the individual straight-chain or branched alkyl moieties.

The formamides of the formula (Va) and their derivatives of the formula (Vb) are generally known compounds of organic chemistry. Formula (VI) provides a general definition of the oxalic acid derivatives required as starting materials for carrying out process (c) according to the invention. In this formula (VI), $R^1$, $R^2$, $R^3$ and X preferably represent those radicals which have already been mentioned in connection with the description of the substances of the formula (I) according to the invention as being preferred for these substituents.

$Y^1$ preferably represents sulphur, or represents a radical

where $R^6$ preferably represents those radicals which have already been mentioned in connection with the description of the substances of the formula (I) according to the invention as being preferred for this substituent.

The oxalic acid derivatives of the formula (VI) are either known (cf., for example, FR 1,306,603) or they can be obtained in analogy to known processes (cf., for example, U.S. Pat. No. 4,321,372; Synthetic Communications 11, 943 [1981], or Organic Reactions 26, 1 [1979]), for example when oxalic esters of the formula (XIII)

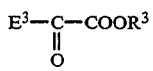 (XIII)

in which
E³ represents alkoxy or halogen, in particular represents methoxy, ethoxy or chlorine, and
R³ has the abovementioned meaning, are reacted with heterocyclic compounds of the formula (XIc)

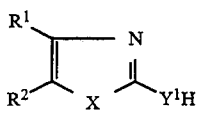 (XIc)

in which
R¹, R², X and Y¹ have the abovementioned meanings, if appropriate in the presence of a diluent, such as, for example, dichloromethane or tetrahydrofuran, and if appropriate in the presence of a base, such as, for example, n-butyllithium, sodium hydride, potassium t-butoxide, triethylamine or pyridine, at temperatures between −80° C. and +80° C.

Oxalic esters of the formula (XIII) are generally known compounds of organic chemistry.

Heterocyclic compounds of the formula (XIc) are likewise generally known or can be obtained in analogy to generally known processes (cf., for example, Organic Reactions 6, 367 et seq., and also the preparation examples).

Formula (VII) provides a general definition of the organometal compounds furthermore required as starting materials for carrying out process (c) according to the invention. In this formula (VII), R⁵ preferably represents those radicals which have already been mentioned in connection with the description of the substances of the formula (I) according to the invention as being preferred for this substituent.

The organometal compounds of the formula (VII) are known (cf., for example, J. org. Chem. 33, 780 [1968]; J. org. Chem. 37, 939 [1972]).

Formula (VIII) provides a general definition of the substituted acrylic esters required as starting materials for carrying out process (d) according to the invention. In this formula (VIII), R¹, R², R³ and X preferably represent those radicals which have already been mentioned in connection with the description of the substances of the formula (I) according to the invention as being preferred for these substituents.

E² preferably represents a suitable acyloxy or sulphonyloxy radical, in particular represents an acetoxy radical, a methanesulphonyloxy radical or a p-toluenesulphonyloxy radical.

The substituted acrylic esters of the formula (VIII) were hitherto unknown.

They are obtained when hydroxyacrylic esters of the formula (IIb)

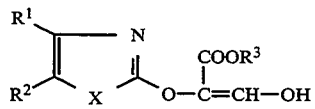 (IIb)

in which

R¹, R², R³ and X have the abovementioned meanings, are reacted with acid chlorides of the formula (XIV)

$R^{10}$-Cl (XIV)

in which
R¹⁰ represents an acyl or sulphonyl radical, in particular represents an acetyl radical, a methane-sulphonyl radical or a p-toluenesulphonyl radical, if appropriate in the presence of a diluent, such as, for example, dichloromethane, and if appropriate in the presence of an acid-binding agent, such as, for example, triethylamine or pyridine, at temperatures between −20° C. and +120° C.

Acid chlorides of the formula (XIV) are generally known compounds of organic chemistry.

Formula (IX) provides a general definition of the thiols furthermore required as starting materials for carrying out process (d) according to the invention. In this formula (IX), R⁵ preferably represents those radicals which have already been mentioned in connection with the description of the substances of the formula (I) according to the invention as being preferred for this substituent.

The thiols of the formula (IX) are generally known compounds of organic chemistry.

Possible diluents for carrying out process (a) according to the invention are inert organic solvents. These include, in particular, aliphatic, alicyclic or aromatic, optionally halogenated hydrocarbons, such as, for example, benzinebenzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or sulphoxide, such as dimethyl sulphoxide.

If appropriate, process (a) according to the invention can also be carried out in a two-phase system, such as, for example, water/toluene or water/dichloromethane, if appropriate in the presence of a phase-transfer catalyst. Examples which may be mentioned of such catalysts are: tetrabutylammonium iodide, tetrabutylammonium bromide, tributyl-methylphosphonium bromide, trimethyl-C₁₃/C₁₅-alkylammoniumchloride, dibenzyl-dimethyl-ammoniummethyl sulphate, dimethyl-C₁₂/C₁₄-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)ethyl]-amine.

Process (a) according to the invention is preferably carried out in the presence of a suitable basic reaction auxiliary. Possible reaction auxiliaries are all inorganic and organic bases which can customarily be used. The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU), are preferably used.

When carrying out process (a) according to the invention, the reaction temperatures can be varied within a substantial range. In general, the process is carried out at temperatures between −30° C. and +120° C., preferably at temperatures between −20° C. and +60° C.

For carrying out process (a) according to the invention, 1.0 to 10.0 moles, preferably 1.0 to 5.0 moles, of alkylating agent of the formula (III) and if appropriate 1.0 to 5.0 moles, preferably 1.0 to 2.0 moles, of reaction auxiliary are generally employed per mole of 3-hydroxyacrylic ester or of a corresponding alkali metal salt of the formula (II). In this connection, it is also possible to prepare the 3-hydroxyacrylic esters or their alkali metal salts of the formula (II) which are required as starting compounds for carrying out process (a) according to the invention, in a preceding reaction directly in the reaction vessel and reacting the product further with the alkylating agent of the formula (III) according to process (a) according to the invention, directly starting from the reaction mixture without isolation ("one-pot process"). The reaction is carried out and the reaction products are worked up and isolated by generally customary methods (cf. also the preparation examples).

Possible diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, or ethers, such as diethyl ether, dioxane, tetrahydrofuran or ethylene glycol dimethyl ether or ethylene glycol diethyl ether.

However, it is also possible to carry out process (b) according to the invention without the addition of a diluent.

When carrying out process (b) according to the invention, the reaction temperatures can be varied within a substantial range. In general, the process is carried out at temperatures between −20° C. and +200° C., preferably at temperatures between 0° C. and 150° C.

For carrying out process (b) according to the invention, 1.0 to 30.0 moles, preferably 1.0 to 15.0 moles of formamide of the formula (Va) or of a corresponding derivative of the formula (Vb) are generally employed per mole of substituted acetic ester of the formula (IV). The reaction is carried out and the reaction products are worked up and isolated by generally customary methods (in this context, cf. also G. Mathieu; J. Weill-Raynal "Formation of C—C Bonds", Vol. I; p. 229–244; Thieme Verlag Stuttgart 1973).

Possible diluents for carrying out process (c) according to the invention are inert organic solvents. These include, in particular, aliphatic, alicyclic or aromatic hydrocarbons, such as, for example, benzine, benzene, toluene, xylene, petroleum ether, hexane or cyclohexane, or ethers, such as diethyl ether, dioxane, tetrahydrofuran or ethylene glycol dimethyl ether or ethylene glycol diethyl ether.

When carrying out process (c) according to the invention, the reaction temperatures can be varied within a substantial range. In general, the process is carried out at temperatures between −100° C. and +100° C., preferably at temperatures between −80° C. and +50° C.

For carrying out process (c) according to the invention, 1.0 to 1.5 moles, preferably 1.0 to 1.2 moles, of an organometal compound of the formula (VII) are generally employed per mole of oxalic acid derivative of the formula (VI). The reaction is carried out, and the reaction products are worked up and isolated by known methods (cf., for example, J. org. Chem. 33, 780 [1968]; J. org. Chem. 37; 939 [1972]).

Possible diluents for carrying out process (d) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (d) according to the invention is preferably carried out in the presence of a suitable reaction auxiliary. Possible reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (d) according to the invention, the reaction temperatures can be varied within a substantial range. In general, the process is carried out at temperatures between −20° C. and 180° C., preferably at temperatures between 0° C. and 150° C.

Depending on the boiling point of the reactants used, for example when lower-boiling thiols of the formula (IX) are used, the process according to the invention can also be carried out under pressure, if desired. In this case, the process is preferably carried out at the pressure which is established under the reaction conditions when the mixture is heated to the reaction temperature required.

For carrying out process (d) according to the invention, 1.0 to 20.0 moles, preferably 1.0 to 5.0 moles, of thiol of the formula (IX) and, if appropriate, 1.0 to 5.0 moles, preferably 1.0 to 1.5 moles, of reaction auxiliary are generally employed per mole of substituted acrylic ester of the formula (VIII). The reaction is carried out and the reaction products are worked up and isolated by generally customary methods. The active compounds according to the invention have a powerful action against pests and can be employed in practice for combating undesired harmful organisms. The active substances are suitable for use as, for example, plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, Pythium ultimum;

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this connection, the active substances according to the invention can be employed with particularly good success for combating cereal diseases, such as, for example, the pathogen causing powdery mildew of cereals (*Erysiphe graminis*) or the pathogen causing net blotch disease of barley (*Pyrenophora teres*) or the patbogen causing eyespot on cereals (*Pseudocercosporella herpotrichoides*) or the pathogen causing glume blotch of wheat (*Leptosphaeria nodorum*), or for combating rice diseases, such as, for example, the pathogen causing rice blast disease (*Pyricularia oryzae*) or the pathogen causing rice stem disease (*Pellicularia sasakii*), or for controlling diseases in fruit and vegetable growing, such as, for example, the pathogen causing apple scab (*Venturia inaequalis*).

Moreover, the active compounds according to the invention show a broad in-vitro activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and frae ionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

In the formulations, the active compounds according to the invention can be present in mixtures with other known active compounds, such as, for example, fungicides, insecticides, acaricides and herbicides, as well as in mixtures of fertilizers and growth regulators.

The active compounds can be used as such, in the form of their formulations or in the use forms prepared from these formulations, such as ready-to-use solutions, suspensions, wettable powders, pastes, soluble powders, dusts and granules. They are applied in a customary manner, for example by watering, spraying, atomizing, scattering, dusting, foaming, brushing on, etc. It is furthermore possible to apply the active substances by the ultra-low-volume process, or to inject the active compound preparation or the active compound itself into the soil. It is also possible to treat the seeds of the plants.

In the treatment of parts of plants, the active compound concentrations in the use forms can be varied within a substantial range. In general, they are between 1 and 0.0001% by weight, preferably between 0.5 and 0.001%.

In the treatment of seeds, amounts of active compound of 0.001 to 50 g per kilogram of seed, preferably 0.01 to 10 g, are generally required.

In the treatment of the soil, active compound concentrations of 0.00001 to 0.1% by weight, preferably of 0.0001 to 0.02%, are required at the site of action.

PREPARATION EXAMPLES

Example 1

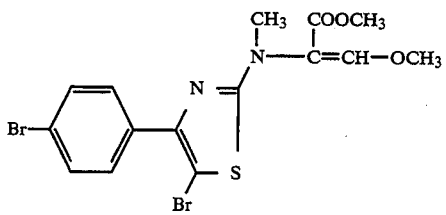

Process (a)—one-pot variant

A solution of 5.4 g (0.013 mol) of methyl N-[5-bromo-4-(4-bromophenyl)-thiazol-2-yl]-N-methylacetate in a mixture of 25 ml of dimethylformamide and 25 ml of methyl formate is added dropwise with stirring and cooling as well as with careful exclusion of moisture to a suspension of 0.8 g (0.0335 mol) of sodium hydride in 75 ml of dimethylformamide, in which process the temperature of the reaction mixture should not exceed 0° C. When the addition is complete, the mixture is stirred for 15 hours at room temperature, 4.9 g (0.039 mol) of dimethyl sulphate are then added, the mixture is stirred for 15 more hours at room temperature, 300 ml of water are then added, the mixture is extracted several times using ethyl acetate, the combined organic phases are dried over sodium sulphate and concentrated under reduced pressure, and the residue is purified by chromatography on silica gel.

This gives 3.0 g (51% of theory) of methyl N-[5-bromo-4-(4-bromophenyl)-thiazol-3-yl]-N-methyl-2-methoxymethylideneglycinate of melting point 112° C.

Example 2

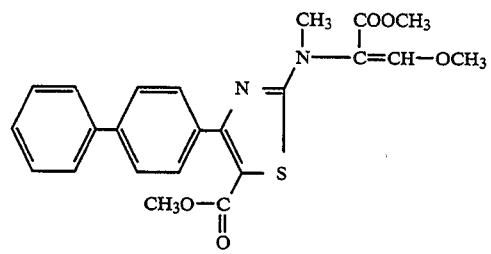

Process (a)—one-pot variant

A solution of 4 g (0.01 mol) of methyl N-[5-methoxycarbonyl-4-(4-biphenylyl)-thiazol-2-yl]-N-methylacetate in a mixture of 10 ml of dimethylformamide and 10 ml of methyl formate is added dropwise with stirring and cooling as well as with careful exclusion of moisture and under an argon protective gas atmosphere to a suspension of 0.66 g (0.022 mol) of sodium hydride in 10 ml of dimethylformamide, during which process the temperature of the reaction mixture should not exceed 0° C. When the addition is complete, the mixture is stirred for a further four to five hours at 0° C., 3 g (0.02 mol) of dimethyl sulphate are then added dropwise with stirring, and the reaction mixture is subsequently allowed to slowly reach room temperature. The mixture is stirred for 12 more hours at room temperature, the reaction mixture is then treated with ice and extracted several times using dichloromethane, the combined organic phases are dried over sodium sulphate and concentrated under reduced pressure, and the residue is purified by chromatography on silica gel (eluent: dichloromethane/ethyl acetate 20:1). This gives:

2.5 g (56.4% of theory) of methyl N-[5-methoxycarbonyl-4-(4-biphenylyl)-thiazol-2-yl]-*N-methyl*-2-methoxymethylideneglycinate as the Z-isomer of melting point 132° C. as fraction 1 and 0.6 g (13.5% of theory) of methyl N-[5-methoxycarbonyl-4-(4-biphenylyl)-thiazol-2-yl]-*N-methyl*-2-methoxymethylideneglycinate as the E-isomer of melting point 223° C.

The following substituted acrylic esters of the general formula (I) are obtained in a corresponding manner and following the general preparation instructions:

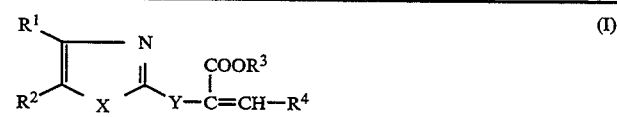

| Example No. | R1 | R2 | R3 | R4 | X | Y | Physical properties |
|---|---|---|---|---|---|---|---|
| 3 | 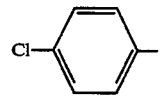 | Br | $CH_3$ | $OCH_3$ | S | —N—<br>\|<br>$CH_3$ | $^1$H-NMR*): 3.26; 3.79; 3.97; 7.46; 7.5; 7.9 |

-continued $$\text{(I)}\quad \begin{array}{c} R^1 \\ \diagdown \\ R^2 \end{array}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! X\!-\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \overset{N}{\underset{\|}{C}}\!\!-Y-\!\!\underset{\|}{C}\!\!=\!CH-R^4,\ \ COOR^3$$

| Example No. | R² | R³ | R⁴ | X | Y | Physical properties |
|---|---|---|---|---|---|---|
| 4 | 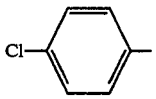 | −C(=O)−H | CH₃ | OCH₃ | S | −N(CH₃)− | ¹H-NMR*): 3.37; 3.8; 4.0; 7.45; 7.5; 7.66; 9.68 |
| 5 | 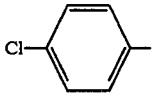 | −CN | CH₃ | OCH₃ | S | −N(CH₃)− | m.p. 129° C. |
| 6 | 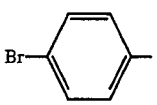 | −C(=O)−H | CH₃ | OCH₃ | S | −N(CH₃)− | ¹H-NMR*) 3.4; 3.8; 7.2–7.7; 9.68 |
| 7 | 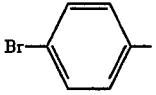 | −CN− | CH₃ | OCH₃ | S | −N(CH₃)− | m.p. 151–152° C. |
| 8 | 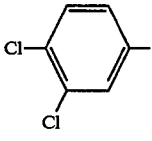 | −Br− | CH₃ | OCH₃ | S | −N(CH₃)− | m.p. 137° C. |
| 9 | 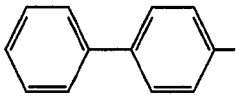 | −Br | CH₃ | OCH₃ | S | −N(CH₃)− | |
| 10 | 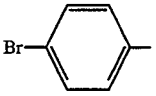 | −Cl | CH₃ | OCH₃ | S | −N(CH₃)− | m.p. 108–110° C. |
| 11 | 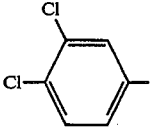 | Cl | CH₃ | OCH₃ | S | −N(CH₃)− | m.p. 136° C. |
| 12 | 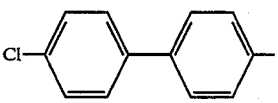 | Br | CH₃ | OCH₃ | S | −N(CH₃)− | |
| 13 | 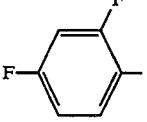 | Br | CH₃ | OCH₃ | S | −N(CH₃)− | m.p. 87–89° C. |
| 14 | 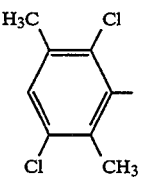 | Br | CH₃ | OCH₃ | S | −N(CH₃)− | m.p. 111–112° C. |

-continued

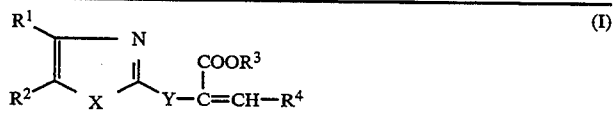
(I)

| Example No. | R² | R³ | R⁴ | X | Y | Physical properties |
|---|---|---|---|---|---|---|
| 15 | 2,4-difluorophenyl | Br | CH₃ | OCH₃ | S | $-\underset{CH_3}{N}-$ | m.p. 77–79° C. |
| 16 | 2,5-dimethoxyphenyl | Br | CH₃ | OCH₃ | S | $-\underset{CH_3}{N}-$ | m.p. 87–88° C. |
| 17 | 4-fluorophenyl | Br | CH₃ | OCH₃ | S | $-\underset{CH_3}{N}-$ | |
| 18 | 4-fluorophenyl | Cl | CH₃ | OCH₃ | S | $-\underset{CH_3}{N}-$ | |
| 19 | 4-methylphenyl | Br | CH₃ | OCH₃ | S | $-\underset{CH_3}{N}-$ | |
| 20 | 4-chlorophenyl | Br | CH₃ | N(CH₃)₂ | S | $-\underset{CH_3}{N}-$ | |
| 21 | 3-bromophenyl | Br | CH₃ | OCH₃ | S | $-\underset{CH_3}{N}-$ | m.p. 76–77° C. |
| 22 | 4-biphenylyl | SCCl₂F | CH₃ | OCH₃ | S | $-\underset{CH_3}{N}-$ | |
| 23 | 3-trifluoromethylphenyl | Br | CH₃ | OCH₃ | S | $-\underset{CH_3}{N}-$ | m.p. 83–87° C. |
| 24 | 4-bromophenyl | SCCl₂F | CH₃ | N(CH₃)₂ | S | $-\underset{CH_3}{N}-$ | m.p. 122–123° C. |
| 25 | 3-chlorophenyl | Br | CH₃ | OCH₃ | S | $-\underset{CH_3}{N}-$ | |

-continued

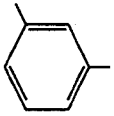

(I)

| Example No. | R² | R³ | R⁴ | X | Y | Physical properties |
|---|---|---|---|---|---|---|
| 26 | 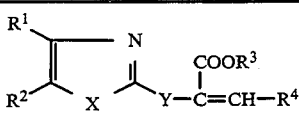 | Cl | CH₃ | OCH₃ | S | —N(CH₃)— | m.p. 94–95° C. |

*)The ¹H-NMR spectra were recorded in deuterochloroform (CDCl₃) with tetramethylsilane (TMS) as the internal standard. The chemical shift is indicated as δ-value in ppm.

*) The ¹H-NMR spectra were recorded in deuterochloroform (CDCl₃) with tetramethylsilane (TMS) as the internal standard. The chemical shift is indicated as δ-value in ppm.

PREPARATION OF THE STARTING COMPOUNDS

Example IV-1

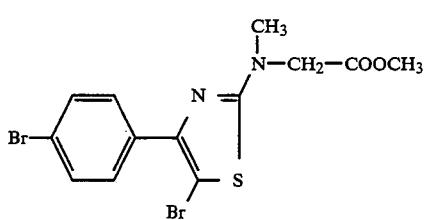

A solution of 2.34 g (0.015 mol) of bromine in 5 ml of glacial acetic acid is added dropwise with stirring in the course of 45 minutes at room temperature to a mixture of 4.5 g (0.013 mol) of methyl N-[4-(4-bromophenyl)-thiazol-2-yl]-N-methylaminoacetate and 2.5 g (0.03 mol) of sodium acetate in 30 ml of glacial acetic acid, the mixture is subsequently stirred with an excess of aqueous saturated sodium hydrogen carbonate solution, and the precipitate which has separated out is filtered off with suction. After drying, 5.4 g (97% of theory) of methyl N-[5-bromo-4-(4-bromophenyl)-thiazol-2-yl]-N-methylaminoacetate are obtained as an oil.

¹H-NMR (CDCl₃/tetramethylsilane):

δ=3.13 (s,3H); 3.75 (s,3H); 4.30 (s,2H); 7.51 (d,2H); 7.80 (d,2H) ppm.

Example IV-2

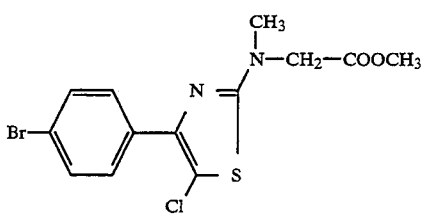

Chlorine gas is passed at 35° C. with stirring into a mixture of 4.5 g (0.013 mol) of methyl N-[4-(4-bromophenyl)-thiazol-2-yl]-N-methylaminoacetate and 2.5 g (0.03 mol) of sodium acetate in 30 ml of glacial acetic acid until starting compound is no longer detectable in the thin-layer chromatogram of the reaction mixture. After this, the mixture is stirred with an excess of aqueous saturated sodium hydrogen carbonate solution and the precipitate which has separated out is filtered off with suction and purified by chromatography on silica gel (eluent:dichloromethane/n-hexane 1:1).

This gives 0.58 g (12% of theory) of methyl N-[5-chloro-4-(4-bromophenyl)-thiazol-2-yl]-N-methylaminoacetate.

MS: m/e 32 376 (M⊕); 317,(base peak; M⊕—COOCH₃).

Example IV-3

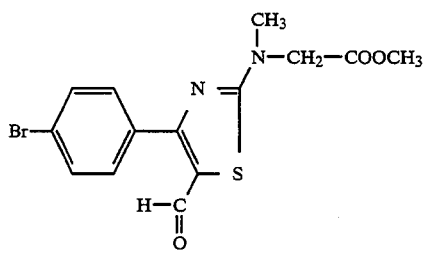

5 g (0.03 mol) of phosphorus oxychloride are added dropwise with stirring and with the exclusion of moisture to a solution of 2.0 g (0.006 mol) of methyl N-[4-(4-bromophenyl)-thiazol-2-yl ]-N-methylaminoacetate in 15 ml of dimethylformamide in such a way that the temperature of the reaction mixture does not exceed 45° C. When the addition is complete, the reaction mixture is allowed to stand for 2 hours at room temperature, it is then poured onto ice, neutralized by adding aqueous sodium hydrogen carbonate solution, and the solids are filtered off and dried.

This gives 1.62 g (71% of theory) of methyl N-[4-(4-bromophenyl)-5-formylthiazol-2-yl]-N-methylaminoacetate as the monohydrate of melting point 105°–106° C.

Example IV-4

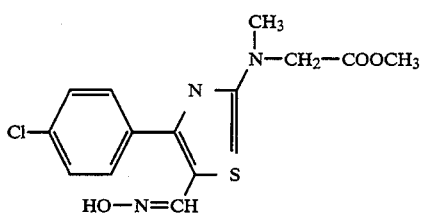

A mixture of 5 g (0.0146 mol) of methyl N-[4-(4-chlorophenyl)-5-formylthiazol-2-yl)-N-methylaminoacetate and 1.6 g (0.023 mol) of hydroxylamine hydrochloride in 50 ml of ethanol and 5 ml of glacial acetic acid is refluxed for 45 minutes with stirring, cooled, poured into ice, neutralized by adding sodium hydrogen carbonate and extracted using ethyl acetate, and the organic phase is dried over sodium sulphate and concentrated under reduced pressure.

This gives 4.56 g (92% of theory) of methyl N-[4-(4-chlorophenyl)-5-hydroximinomethylthiazol-2-yl]-N-methylacetate of melting point 147° C. to 149° C. as a Z/E-isomer mixture.

Example IV-5

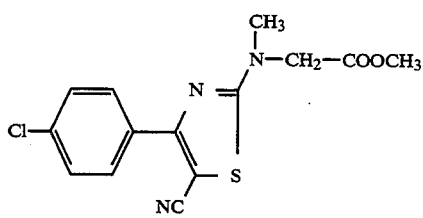

A mixture of 4.16 g (0.0122 mol) of methyl N-[4-(4-chlorophenyl)-5-hydroximinomethylthiazol-2-yl]-N-methyl-aminoacetate and 30 ml of acetic anhydride is refluxed for 4 hours with stirring, cooled, poured into ice-water, neutralized in the cold using saturated aqueous sodium hydrogen carbonate solution and extracted using ethyl acetate, the organic phase is dried over sodium sulphate and concentrated and the crystalline residue is purified by stirring with a mixture of diisopropyl ether and n-hexane.

Filtering off with suction and drying gives 3.01 g (77% of theory) of methyl N-[4-(4-chlorophenyl)-5-cyanothiazol-2-yl]-N-methylaminoacetate.

MS: m/e=321 (M⊕); 262 (base peak; M⊕—COOCH₃).

Example IV-6

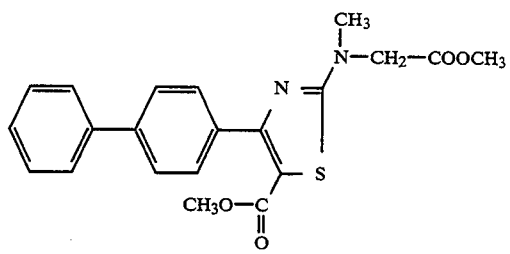

0.9 g (0.03 mol) of sodium hydride is added in portions with stirring and cooling to a mixture of 8.1 g (0.025 mol) of methyl 2-(N-methylamino)-4-(4-biphenylyl)-thiazol-5-yl-carboxylate and 30 ml of dimethylformamide in such a way that the temperature of the reaction mixture does not exceed 20° C. The mixture is subsequently stirred for 45 minutes at room temperature, 18.3 g (0.119 mol) of methyl bromoacetate are then added dropwise in the course of 30 minutes with stirring at room temperature; when the addition is complete, the reaction mixture is stirred for a further 12 hours at room temperature, then poured into ice-water and extracted several times using dichloromethane, the combined organic phases are dried over sodium sulphate and concentrated under reduced pressure, and the crystalline residue is purified by stirring with diisopropyl ether.

This gives 5.1 g (52% of theory) of methyl N-[4-(4-biphenylyl)-5-methoxycarbonylthiazol-2-yl]-N-methylamino-acetate of melting point 141° C.

The following substituted acetic esters of the general formula (IV)

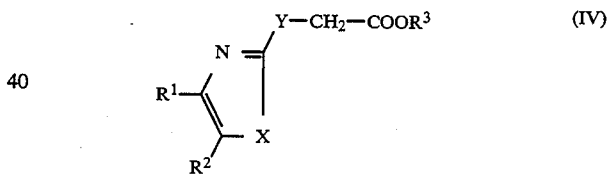

are obtained in a corresponding manner and following the general preparation instructions.

| Example No. | R¹ | R² | R³ | X | Y | Melting point/°C |
|---|---|---|---|---|---|---|
| IV-7 | Cl-⟨phenyl⟩- | Br | CH₃ | S | —N(CH₃)— | 92–94 |
| IV-8 | Cl-⟨phenyl⟩- | —C(O)—H | CH₃ | S | —N(CH₃)— | 115–118 |
| IV-9 | ⟨biphenyl⟩- | Br | CH₃ | S | —N(CH₃)— | 105–106 |

-continued

| Example No. | R¹ | R² | R³ | X | Y | Melting point/°C |
|---|---|---|---|---|---|---|
| IV-10 | 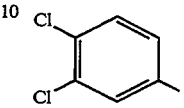 | Br | CH₃ | S | —N—<br>\|<br>CH₃ | 109 |
| IV-11 | 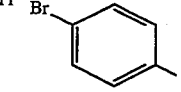 | CN | CH₃ | S | —N—<br>\|<br>CH₃ | 133–136 |

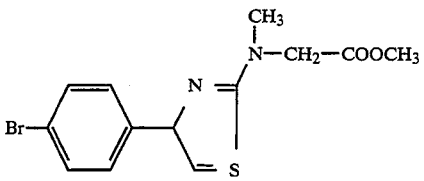

A solution of 9.0 g (0.036 mol) of 4-(4-bromophenyl)-2-methylaminothiazole in 50 ml of dimethylformamide is added dropwise with stirring and with the exclusion of moisture and ice cooling to 2.73 g (0.114 mol) of sodium hydride in 200 ml of dimethylformamide in such a way that the temperature of the reaction mixture does not exceed 10° C. When the addition is complete, the mixture is stirred for one hour at room temperature and then cooled to 10° C, and 21.4 g (0.14 mol) of methyl bromoacetate are then added dropwise with stirring in the course of one hour, the reaction mixture is subsequently stirred for 15 hours at room temperature and then transferred into ice-water, the mixture is extracted several times using dichloromethane, the combined organic phases are dried over sodium sulphate and concentrated under reduced pressure, and the residue is purified by chromatography on silica gel (eluent: dichloromethane).

This gives 10.0 g (42% of theory) of methyl N-[4-(4-bromophenyl)-thiazol-2-yl]-N-methyl-aminoacetate of melting point 95° C.

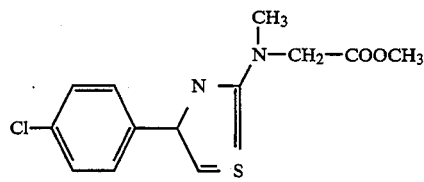

is obtained in a corresponding manner and following the general preparation instructions, melting point 86° C.

Example XI-1

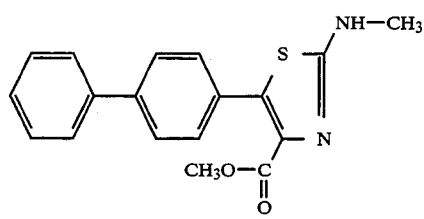

A mixture of 17.1 g (0.06 mol) of methyl 2-chloro-2-(4-phenylbenzoyl)-acetate (by chlorination with sulphuryl chloride following standard procedures; cf. also DE-OS (German Published Specification) 2,343,974), 10.8 g (0.12 mol) of N-methylthiourea and 200 ml of methanol is refluxed for 3 hours, cooled and stirred into an excess of dilute aqueous sodium hydrogen carbonate solution, and the precipitate which has separated out is filtered off with suction and dried.

This gives 18.2 g (95% of theory) of methyl 2-(N-methylamino-4-(4-biphenylyl)-thiazol-5-ylcarboxylate of melting point >230° C.

Example XI-2

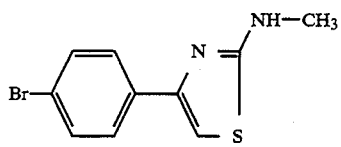

A mixture of 27.8 g (0.1 mol) of 2,4'-dibromoacetophenone (cf., for example, Tetrahedron Lett. 1975, 373–376), 9.0 g (0.115 mol) of N-methylthiourea and 400 ml of ethanol is refluxed for 3 hours, subsequently cooled and transferred into an excess of dilute aqueous sodium hydrogen carbonate solution, the reaction mixture is extracted using dichloromethane, and the combined organic phases are dried over sodium sulphate and concentrated.

This gives 20.8 g (78% of theory) of 2-(N-methylamino)-4-(4-bromophenyl)-thiazole of melting point 147 ° C.

Example XI-3 is obtained in a corresponding manner:

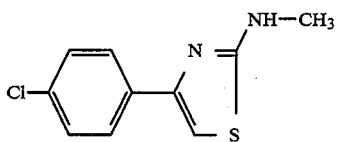

Melting point 140° C.

Use Examples

In the use examples which follow, the compound indicated below was employed as the comparison substance:

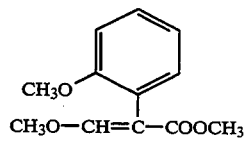

(A)

Methyl 3-methoxy-2-(2-methylphenyl)-acrylate (disclosed in EP 178,826).

Example A

Venturia test (apple)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the pathogen causing apple scab (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to Preparation Examples 1 and 3.

Example B

Pyrenophora teres test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compound according to Preparation Example 3.

Example C

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test a clearly superior activity compared with the prior art is shown, for example, by the compounds according to Preparation Examples 1 and 3.

It is understood that the specification and examples are illustrative but not limitative of the present invention and that other embodiments within the spirit and scope of the invention will suggest themselves to those skilled in the art.

We claim:

1. A substituted acetic ester of the formula

(IVa)

in which
$Y^2$ represents oxygen or sulphur, or represents an N-alkyl radical which is straight-chain or branched and has 1 to 6 carbon atoms,
$R^1$ represents hydrogen, or represents straight-chain or branched alkyl having 1 t6 8 carbon atoms, or represents straight-chain or branched alkenyl having 2 to 8 carbon atoms, or represents aralkyl having 1 to 6 carbon atoms in the straight-chain or branched alkyl moiety, aralkenyl having 2 to 6 carbon atoms in the straight-chain or branched alkenyl moiety or aryl having 6 to 10 carbon atoms in the respective aryl moiety, each of which is optionally monosubstituted to polysubstituted in the aryl moiety by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, double-linked alkanediyl having 3 to 5 carbon atoms, or aryl, aralkyl, aryloxy or aralkyloxy, each of which has 6 to 10 carbon atoms in the aryl moiety and if appropriate 1 to 4 carbon atoms in the straight-chain or branched alkyl moiety and each of which is optionally monosubstituted to polysubstituted in the aryl moiety by identical or different substituents from the group consisting of halogen, alkyl, alkoxy, alkylthio, halogenoalkyl, halogenoalkoxy and halogenoalkylthio, each having 1 to 4 carbon atoms and if appropriate 1 to 9 identical or different halogen atoms, or heteroarylalkyl or heteroaryl, each of which has 2 to 9 carbon atoms and 1 to 4 identical or different hetero atoms in the heteroaryl moiety and if appropriate 1 to 4 carbon atoms in the straight-chain or branched alkyl moiety and each of which is optionally monosubstituted to polysubstituted in the heteroaryl moiety by identical or different substituents from the group consisting of halogen, alkyl, alkoxy, alkylthio, halogenoalkyl, halogenoalkoxy and halogenoalkylthio, each having 1 to 4 carbon atoms and if appropriate 1 to 9 identical or different halogen atoms;

R¹ furthermore represents a heteroaryl radical which has 2 to 9 carbon atoms and 1 to 4 identical or different hetero atoms and which is optionally monosubstituted to polysubstituted by identical or different substituents, possible substituents being the abovementioned aryl substituents, R² represents fluorine, chlorine, bromine, iodine, cyano, nitro or formyl, or represents straight-chain or branched halogenoalkyl having 1 to 4 carbon atoms and 1 to 9 identical or different halogen atoms, or represents in each case straight-chain or branched alkoxyalkyl or alkylthioalkyl, each of which has 1 to 4 carbon atoms in the individual alkyl moieties, or represents in each case straight-chain or branched hydroximinoalkyl, alkoximinoalkyl, N-alkyliminoalkyl or N,N-dialkylhydrazonoalkyl, each of which has 1 to 4 carbon atoms in the individual alkyl moieties, or represents in each case straight-chain or branched alkoxy or alkylthio, each of which has 1 to 4 carbon atoms, or represents in each case straight-chain or branched halogenoalkoxy or halogenoalkylthio, each of which has 1 to 4 carbon atoms and each of which has 1 to 9 identical or different halogen atoms, or represents in each case straight-chain or branched alkanoyl or N,N-dialkylcarbamoyl, each of which has 1 to 4 carbon atoms in the individual alkyl moieties, or represents heterocyclylcarbonyl, the heterocyclyl radical being a saturated five- to seven-membered N-linked heterocyclic ring which can optionally contain a further hetero atom and which can optionally be monosubstituted to tetrasubstituted by methyl and/or ethyl;

R² furthermore represents N-aryliminoalkyl, aryloxy or arylthio, each of which is optionally monosubstituted to polysubstituted in the aryl moiety by identical or different substituents, each of which has 6 to 10 carbon atoms, the straight-chain or branched alkyl moiety having 1 to 4 carbon atoms and possible aryl substituents in each case being: halogen, cyano, nitro, in each case straight-chain or branched alkyl, alkoxy or alkylthio, each of which has 1 to 4 carbon atoms-, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, or phenyl which is optionally monosubstituted to polysubstituted by identical or different substituents from the group consisting of halogen and/or straight-chain or branched alky having 1 to 4 carbon atoms, and R³ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted to polysubstituted in the aryl moiety by identical or different substituents, possible aryl substitu ents being those mentioned in the case of R¹.

X represents oxygen or sulphur, and

Y² represents oxygen or sulphur or represents a radical

where

R⁶ represents straight-chain or branched alkyl having 1 to 6 carbon atoms.

2. A substituted acetic ester according to claim 1, in which

R¹ represents hydrogen, methyl, ethyl, n- or i-propyl or n-, i-, s- or t-butyl, or represents allyl or n- or i-butenyl, or represents benzyl, phenylethyl, phenylethenyl, phenyl, naphthyl, pyridyl, thienyl or furyl, each of which is optionally monosubstituted to tetrasubstituted in the aryl moiety or in the heteroaryl moiety by identical or different substituents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxy-carbonyl, methoximinomethyl, ethoximinomethyl, methoximinoethyl, ethoximinoethyl, cyclopentyl, cyclohexyl, 1,3-propanediyl or 1,4-butanediyl, and phenyl, benzyl, phenoxy or benzyloxy, each of which is optionally monosubstituted to trisubstituted in the phenyl moiety by identical or different substituents from the group consisting of fluorine, chlorine, bromine, methyl, ethyl, methoxy, ethoxy, methylthio, trifluoromethyl, difluoromethoxy, trifluoromethoxy and/or trifluoromethylthio, R² represents chlorine, bromine, iodine, cyano, nitro, formyl, chloromethyl, bromomethyl, iodomethyl, methoxymethyl, ethoxymethyl, n- or i-propoxymethyl, methylthiomethyl, ethylthiomethyl or n- or i-propylthiomethyl, or represents hydroximinomethyl, hydroximinoethyl or hydroximinopropyl, or represents methoximinomethyl, ethoximinomethyl, n- or i-propoximinomethyl, methoximinoethyl, ethoximinoethyl or n- or i-propoximinoethyl, or represents methyliminomethyl, ethyliminomethyl or n- or i-propyliminomethyl, or represents methyliminoethyl, ethyliminoethyl or n- or i-propyliminoethyl, or represents N,N-dimethylhydrazonomethyl, N,N-diethylhydrazonomethyl, N-methyl-N-ethylhydrazonomethyl, N-methyl-N-propylhydrazonomethyl, N,N-dipropylhydrazonomethyl, N,N-dimethylhydrazonoethyl or N,N-diethylhydrazonoethyl, or represents methoxy, ethoxy, n- or i-propoxy, methylthio, ethylthio or n- or i-propylthio, or represents trifluoromethoxy, difluoromethoxy, dichlorofluoromethoxy, difluorochloromethoxy, trichloromethoxy, trifluoromethylthio, trichloromethylthio, difluoromethylthio, dichlorofluoromethylthio or difluorochloromethylthio or represents acetyl, propionyl, butyryl, methoxycarbonyl, ethoxycarbonyl, n- or i-propoxycarbonyl, N,N-dimethylaminocarbonyl, N,N-diethylaminocarbonyl, N,N-dipropylaminocarbonyl, N-methyl-N-ethylaminocarbonyl or N-methyl-N-propylaminocarbonyl, or represents 1-piperidinylcarbonyl or 4-morpholinylcarbonyl, or represents N-phenyliminomethyl, N-phenyliminoethyl, phenoxy or phenylthio, each of which is optionally monosubstituted to trisubstituted in the phenyl moiety by identical or different substituents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoximinomethyl, ethoximinomethyl, methoximinoethyl or ethoximinoethyl, and phenyl which is optionally monosubstituted to trisubstituted by identical or different substituents from the group consisting of fluorine, chlorine, bromine, methyl and/or ethyl, $R^3$ represents methyl, ethyl, n- or i-propyl or n-, i-, s- or t-butyl, or represents benzyl which is optionally monosubstituted to trisubstituted by identical or different substituents, possible substituents being those mentioned in the case of $R^1$, X represents oxygen or sulphur and $Y^2$ represents oxygen or sulphur, or represents a radical

where $R^6$ represents methyl, ethyl, n- or i-propyl or n-, i-, s- or t-butyl.

3. A substituted acetic ester according to claim 1, in which $R^1$ represents hydrogen, methyl, ethyl, or n- or i-propyl, or represents phenyl or naphthyl, each of which is optionally monosubstituted to tetrasubstituted by identical or different substituents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl ethoximinomethyl, methoximinoethyl, ethoximinoethyl, cyclopentyl, cyclohexyl, 1,3-propanediyl or 1,4-butanediyl, and phenyl, phenoxy, benzyl or benzyloxy, each of which is optionally monosubstituted or disubstituted by identical or different substituents from the group consisting of fluorine, chlorine, bromine, methyl and/or ethyl, $R^2$ represents chlorine, bromine, cyano, nitro, formyl, methoxymethyl, ethoxymethyl, methylthiomethyl, hydroximinomethyl, methoximinomethyl, ethoximinomethyl, methyliminomethyl, ethyliminomethyl, N,N-dimethylhydrazonomethyl or N,N-diethylthydrazonomethyl, or represents methoxy, ethoxy, methylthio, ethylthio, trifluoromethylthio, dichlorofluoromethylthio, difluorochloromethylthio or trichloromethylthio, or represents acetyl, N,N-dimethylaminocarbonyl, N,N-diethylaminocarbonyl or N-methyl-N-ethylaminocarbonyl, or represents phenylthio which is optionally monosubstituted or disubstituted by identical or different substituents from the group consisting of fluorine, chlorine, bromine, cyano, nitro, methyl, ethyl, n- or i-propyl, n-, i-, s- or butyl, methoxy, ethoxy, n-or i-propoxy, methylthio, trifluoromethyl, trifluoromethoxy and trifluoromethylthio, $R^3$ represents methyl, ethyl or benzyl, X represents oxygen or sulphur and represents oxygen or sulphur, or represents a radical

where $R^6$ represents methyl or ethyl.

4. A substituted acetic ester according to claim 1, in which $R^1$ represents hydrogen, methyl, ethyl or n- or i-propyl, or represents phenyl which is optionally monosubstituted or disubstituted by identical or different substituents, from the group consisting of fluorine, chlorine, bromine, cyano, nitro, methyl, ethyl, methoxy ethoxy, methylthio, trifluoromethyl, trifluoromethyoxy, trifluoromethylthio, methoximinomethyl, cyclopentyl, 1,3-propanediyl, methoximinoethyl and phenyl, phenoxy, benzyl or benzyloxy, eahc of which is optionally monosubsituted or disubstituted by identical or different sustituents from the group consisting of fluorine, chlorine, bromine and methyl, $R^2$ represents chlorine, bromine, cyano, nitro, formyl, methoxymethyl, methylthiomethy, methoxycarbonyl, ethoxycarbonyl, methylthiomethyl, methoxycarbonyl, ethoxycarbonyl, methylthio, trifluoromethylthio or methoxyiminomethyl, $R^3$ represents methyl or ethyl, X represents oxygen or sulphur and $Y^2$ represetns an N-methyl radical.

5. A compound according to claim 1, of the formula

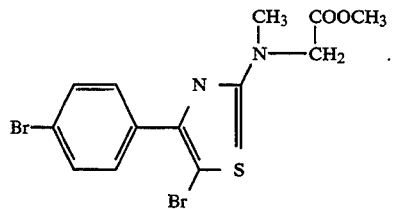

6. A compound according to claim 1, of the formula

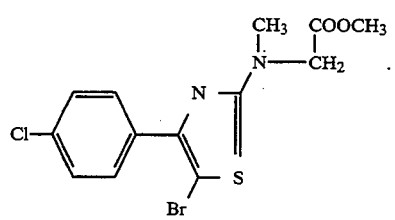

7. A compound according to claim 1, of the formula

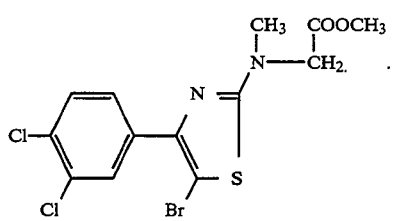

8. A substituted acetic ester of the formula

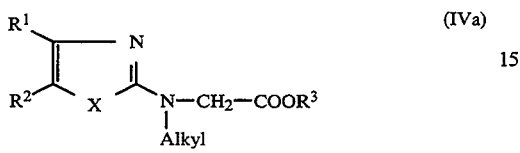

in which

Alkyl is straight-chain or branched and has 1 to 6 carbon atoms,

R¹ represents hydrogen, or represents straight-chain or branched alkyl having 1 to 8 carbon atoms, or represents straight-chain or branched alkenyl having 2 to 8 carbon atoms, or represents aralkyl having 1 to 6 carbon atoms in the straight-chain or branched alkyl moiety, aralkenyl, having 2 to 6 carbon atoms in the straight-chain or branched alkenyl moiety or aryl having 6 to 10 carbon atoms in the respective aryl moiety, each of which is optionally monosubstituted to polysubstituted in the aryl moiety by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkorycarbonyl or alkoximinoalkyl, each of which has 1 to 8 carbon atoms in the individual alkyl moieties, cycloalkyl having 3 to 7 carbon atoms, double-linked alkanediyl having 3 to 5 carbon atoms, or aryl, aralkyl, aryloxy or aralkyloxy, each of which has 6 to 10 carbon atoms in the aryl moiety and if appropriate 1 to 4 carbon atoms in the straight-chain or branched alkyl moiety and each of which is optionally monosubstituted to polysubstituted in the aryl moiety by identical or different substituents from the group consisting of halogen, alkyl, alkoxy, alkylthio, halogenoalkyl, halogenoalkoxy and halogenoalkylthio, each having 1 to 4 carbon atoms and if appropriate 1 to 9 identical or different halogen atoms, or heteroarylalkyl or heteroaryl, each of which has 2 to 9 carbon atoms and 1 to 4 identical or different hetero atoms in the heteroaryl moiety and if appropriate 1 to 4 carbon atoms in the straight-chain or branched alkyl moiety and each of which is optionally monosubstituted to polysubstituted in the heteroaryl moiety by identical or different substituents from the group consisting of halogen, alkyl, alkoxy, alkylthio, halogenoalkyl, halogenoalkoxy and halogenoalkylthio, each having 1 to 4 carbon atoms and if appropriate 1 to 9 identical or different halogen atoms;

R¹ furthermore represents a heteroaryl radical which has 2 to 9 carbon atoms and 1 to 4 identical or different hetero atoms and which is optionally monosubstituted to polysubstituted by identical or different substituents, possible substituents being the abovementioned aryl substituents, R² represents fluorine, chlorine, bromine, iodine, cyano, nitro or formyl, or represents straight-chain or branched halogenoalkyl having 1 to 4 carbon atems and 1 to 9 identical or different halogen atoms, or represents in each case straight-chain or branched alkoxyalkyl or alkylthioalkyl, each of which has 1 to 4 carbon atoms in the individual alkyl moieties, or represents in each case straight-chain or branched hydroximinoalkyl, alkoximinoalkyl, N-alkyliminoalkyl or N, N-dialkylhydrazonoalkyl, each of which has 1 to 4 carbon atoms in the individual alkyl moieties, or represents in each case straight-chain or branched alkoxy or alkylthio, each of which has 1 to 4 carbon atoms, or represents in each case straight-chain or branched halogenoalkoxy or halogenoalkylthio, each of which has 1 to 4 carbon atoms and each of which has 1 to 9 identical or different halogen atoms, or represents in each case straight-chain or branched alkanoyl, alkoxycarbonyl or N, N-dialkylcarbamoyl, each of which has 1 to 4 carbon atoms in the individual alkyl moieties, or represents heterocyclylcarbonyl, the heterocyclyl radical being a saturated five- to seven-membered N-linked heterocyclic ring which can optionally contain a further hetero atom and which can optionally be monosubstituted to tetrasubstituted by methyl and/or ethyl;

R² furthermore represents N-aryliminoalkyl, aryloxy or arylthio, each of which is optionally monosubstituted to polysubstituted in the aryl moiety by identical or different substituents, each of which has 6 to 10 carbon atoms, the straight-chain or branched alkyl moiety having 1 to 4 carbon atoms and possible aryl substituents in each case being: halogen, cyano, nitro, in each case straight-chain or branched alkyl, alkoxy or alkylthio, each of which has 1 to 4 carbon atoms, in each case snraight-chain or branched halogenoalk-yl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, or phenyl which is optionally monosubstituted to polysubstituted by identical or different substituents from the group consisting of halogen and/or straight-chain or branched alky having 1 to 4 carbon atoms, and R³ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted to polysubstituted in the aryl moiety by identical or different substituents, possible aryl substituents being those mentioned in the case of R¹.

9. A substituted acetic ester according to claim 1, in which

R¹ represents hydrogen, methyl, ethyl, n- or i-propyl or n-, i-, s- or t-butyl, or represents allyl or n- or i-butenyl, or represents benzyl, phenylethyl, phenylethenyl, phenyl, naphthyl, pyridyl, thienyl or furyl, each of which is optionally monosubstituted to tetrasubstituted in the aryl moiety or in the heteroaryl moiety by identical or different substituents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxy-carbonyl, methoximinomethyl, ethoximinomethyl, methoximinoethyl, ethoximinoethyl, cyclopentyl, cyclohexyl, 1,3-propanediyl or 1,4-butanediyl, and phenyl, benzyl, phenoxy or benzyloxy, each of which is optionally monosubstituted to trisubstituted in the phenyl moiety by identical or different substituents from the group consisting of fluorine, chlorine, bromine, methyl, ethyl, methoxy, ethoxy, methylthio, trifluoromethyl, difluoromethoxy, trifluoromethoxy and/or trifluoromethylthio, $R^2$ represents chlorine, bromine, iodine, cyano, nitro, formyl, chloromethyl, bromomethyl, iodomethyl, methoxymethyl, ethoxymethyl, n- or i-propoxymethyl, methylthiomethyl, ethylthiomethyl or n- or i-propylthiomethyl, or represents hydroximinomethyl, hydroximinoethyl or hydroximinopropyl, or represents methoximinomethyl, ethoximinomethyl, n- or i-propoximinomethyl, methoximinoethyl, ethoximinoethyl or n- or i-propoximinoethyl, or represents methyliminomethyl, ethyliminomethyl or n- or i-propyliminomethyl, or represents methyliminoethyl, ethyliminoethyl or n- or i-propyliminoethyl, or represents N,N-dimethylhydrazonomethyl, N,N-diethylhydrazonomethyl, N-methyl-N-ethylhydrazonomethyl, N-methyl-N-propylhydrazonomethyl, N,N-dipropylhydrazonomethyl, N,N-dimethylhydrazonoethyl or N,N-diethylhydrazonoethyl, or represents methoxy, ethoxy, n- or i-propoxy, methylthio, ethylthio or n- or i-propylthio, or represents trifluoromethoxy, difluoromethoxy, dichlorofluoromethoxy, difluorochloromethoxy, trichloromethoxy, tricluoromethylthio, trichloromethylthio, difluoromethylthio, dichlorofluoromethylthio or difluorochloromethylthio or represents acetyl, propionyl, butyryl, methoxycarbonyl, ethoxycarbonyl, n- or i-propoxycarbonyl, N,N-dimethylaminocarbonyl, N,N-diethylaminocarbonyl, N,N-dipropylaminocarbonyl, N-methyl-N-ethylaminocarbonyl or N-methyl-N-propylaminocarbonyl, or represents 1-piperidinylcarbonyl or 4-morpholinylcarbonyl, or represents N-phenyliminomethyl, N-phenyliminoethyl, phenoxy or phenylthio, each of which is optionally monosubstituted to trisubstituted in the phenyl moiety by identical or different substituents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoximinomethyl, ethoximinomethyl, methoximinoethyl or ethoximinoethyl, and phenyl which is optionally monosubstituted to trisubstituted by identical or different substituents from the group consisting of fluorine, chlorine, bromine, methyl and/or ethyl, represents methyl, ethyl, n- or i-propyl or n-, i-, s- or t-butyl, or represents benzyl which is optionally monosubstituted to trisubstituted by identical or different substituents, possible substituents being those mentioned in the case of $R^1$.

10. A substituted acetic ester according to claim 8, in which $R^1$ represents hydrogen, methyl, ethyl, or n- or i-propyl, or represents phenyl or naphthyl, each of whcih is optionally monosubstituted to tetrasubstituted by identical or different substiuents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethyoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3,-propanediyl or 1,4-butanediyl, and phenyl, phenoxy, benzyl or benzyloxy, each of which is optionally monosubstituted or disubstituted by identical or different substituents from the group consisting of fluorine, chlorine, bromine, methyl and-/or ethyl, $R^1$ represents chlorine, bromine, cyano, nitro, formyl, methoxymethyl, ethoxymethyl, methylthiomethyl, hydroximinomethyl, methoximinomethyl, ethoximinomethyl, mehtyliminomethyl, ethyliminomethyl, N,N-dimethylhydrazonomethyl or N,N-diethylthydrazonomethyl, or represents methoxy, ethoxy, methylthio, ethylthio, trifluoromethylthio, dichlorofluoromethylthio, difluorochloromethylthio or trichloromethylthio, or represents acetyl, methoxycarbonyl, ethoxycarbonyl, N,N-dimethylaminocarbonyl, N-N-diethylaminocarbonyl or N-methyl-N-ethylaminocarbonyl, or represetns phenylthio which is optionally monosubstituted or disubstituted by identical or different substitutents from the group consisting of fluorine, chlorine, bromine, cyano, nitro, methyl, ethyl, n- or i-propyl, n-, i-, s- or t-butyl, methoxy, ehtoxy, n- or i-propoxy, methylthio, trifluoromethyl, trifluoromethoxy and trifluoromethylthio, and $R^3$ represents methyl, ethyl or benzyl.

11. A substituted acetic ester according to claim 8, in which $R^1$ represents hydrogen, methyl, ethyl or n- or i-propyl, or represents phenyl which is optionally monosubstituted or disubstituted by identical or different substituents, possible substituents being: fluorine, chlorine, bromine, cyano, nitro, methyl, ethyl, methoxy, ethoxy, methylthio, trifluoromethyl, trifluoromethoxy, trifluoromethylthio, methoxycarbonyl, ethoxycarbonyl, methoximinomethyl, cyclopentyl, 1,3-propanediyl, methoximinoethyl or phenyl, phenoxy, benzyl or benzyloxy, each of which is optionally monosubstituted or disubstituted by identical or different substituents from the series comprising fluorine, chlorine, bromine or methyl, $R^2$ represents chlorine, bromine, cyano, nitro, formyl, methoxymethyl, methylthiomethyl, methoxycarbonyl, ethoxycarbonyl, methylthio, trifluoromethylthio or methoximinomethyl, and $R^3$ represents methyl or ethyl.

* * * * *

UNITED STATES PATENT AND TRADEMARK OFFICE
CERTIFICATE OF CORRECTION

PATENT NO. : 5,412,100  
DATED : May 2, 1995  
INVENTOR(S) : Klausener, et al.

Page 1 of 2

It is certified that error appears in the above-indentified patent and that said Letters Patent is hereby corrected as shown below:

| | |
|---|---|
| Col. 50, line 40 | Delete " t6 " and substitute -- to -- |
| Col. 54, line 8 | Before " butyl " insert -- t- -- |
| Col. 54, line 13 | Before " represents oxygen " insert -- y² -- |
| Col. 54, line 32 | Delete " eahc " and substitute -- each -- |
| Col. 54, lines 39-40 | Delete " ethoxycarbonyl, methylthiomethyl, methoxycarbonyl " |
| Col. 55, line 42 | Delete " alkorycarbonyl " and substitute -- alkoxycarbonyl -- |
| Col. 56, line 10 | Delete " atems " and substitute -- atoms -- |
| Col. 56, line 43, delete "snraight" and substitute --straight--. | |
| Col. 56, line 44 | Delete " halogenoalk-yl " and substitute -- halogenoalkyl -- |
| Col. 57, line 43 | Delete " tricluoromethylthio " and substitute -- trifluoromethylthio -- |
| Col. 57, line 53 | Delete " N-phenyliminomethyl " and substitute -- phenyliminomethyl -- |
| Col. 57, line 67, last line | After ethyl, " insert -- and R³ -- |

UNITED STATES PATENT AND TRADEMARK OFFICE
CERTIFICATE OF CORRECTION

PATENT NO.   : 5,412,100
DATED        : May 2, 1995
INVENTOR(S)  : Klausener, et al.

It is certified that error appears in the above-indentified patent and that said Letters Patent is hereby corrected as shown below:

| | |
|---|---|
| Col. 58, line 29 | Delete " mehtyliminomethyl " and substitute -- methyliminomethyl -- |
| Col. 58, line 43 | Delete " ehtoxy " and substitute -- ethoxy -- |
| Col. 58, line 52 | Delete " possible substitutents being " and substitute -- from the group consisting of -- |
| Col. 58, line 57 | Delete " or " and substitute -- and -- |
| Col. 58, line 61 | Delete " series comprising " and substitute -- group consisting of --, delete " or " and substitute -- and -- |

Signed and Sealed this

Eighth Day of August, 1995

Attest:

BRUCE LEHMAN

*Attesting Officer*   *Commissioner of Patents and Trademarks*